US008764669B2

(12) United States Patent
Inoue

(10) Patent No.: US 8,764,669 B2

(45) Date of Patent: Jul. 1, 2014

(54) BLOOD PRESSURE INFORMATION DISPLAY DEVICE, BLOOD PRESSURE INFORMATION DISPLAY SYSTEM, BLOOD PRESSURE INFORMATION DISPLAY METHOD, AND RECORDING MEDIUM RECORDED WITH BLOOD PRESSURE INFORMATION DISPLAY PROGRAM

(75) Inventor: Tomonori Inoue, Kyoto (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 735 days.

(21) Appl. No.: 13/017,923

(22) Filed: Jan. 31, 2011

(65) Prior Publication Data

US 2011/0130667 A1 Jun. 2, 2011

Related U.S. Application Data

(63) Continuation of application No. PCT/JP2009/066258, filed on Sep. 17, 2009.

(30) Foreign Application Priority Data

Oct. 6, 2008 (JP) ................................ 2008-259891

(51) Int. Cl.
*A61B 5/02* (2006.01)

(52) U.S. Cl.
USPC .......................................... 600/490; 600/493

(58) Field of Classification Search
USPC ................................ 600/485, 490, 494, 493
See application file for complete search history.

(56) References Cited

U.S. PATENT DOCUMENTS

2002/0052554 A1* 5/2002 Yokozeki ..................... 600/490

FOREIGN PATENT DOCUMENTS

| | | |
|---|---|---|
| JP | A-7-236617 | 9/1995 |
| JP | A-11-4813 | 1/1999 |
| JP | A-2002-272689 | 9/2002 |

OTHER PUBLICATIONS

International Search Report for International Patent Application No. PCT/JP2009/066258, mailed on Oct. 20, 2009.

* cited by examiner

*Primary Examiner* — Navin Natnithithadha
*Assistant Examiner* — Etsub Berhanu
(74) *Attorney, Agent, or Firm* — Oliff PLC

(57) ABSTRACT

A blood pressure information display device for calculating a blood pressure value based on a pulse wave amplitude through the oscillometric method and the like, and displaying the calculated blood pressure value as blood pressure information performs a process of changing a magnitude of a specified pulse wave amplitude of a plurality of extracted pulse wave amplitudes according to the operation by a user (medical staff) when a predetermined instruction is input. A predetermined algorithm is applied to the plurality of pulse wave amplitudes reflecting the change to calculate a reference blood pressure value, and the calculated reference blood pressure value is displayed as the blood pressure information.

14 Claims, 17 Drawing Sheets

[mmHg] 70 60 (A)
[mmHg] 71 62 (B)
[mmHg] 71 621 (C)
[mmHg] 71 (D)

33 Oscillation Circuit
43 Flash Memory
100
102 Drive Control Unit
103 Acquiring Unit
104 Pulse Wave Amplitude Extracting Unit
106 Blood Pressure Calculating Unit
108 Display Processing Unit
40 Display Unit
112 Change Processing Unit
53 Pump Drive Circuit
54 Valve Drive Circuit
41 Operation Unit

| Time Data | Cuff Pressure Data | Actual Measurement Amplitude Data | Processed Amplitude Data |
|---|---|---|---|
| 1 | PC(1) | AM(1) | – (NULL) |
| 2 | PC(2) | AM(2) | – |
| 3 | PC(3) | AM(3) | – |
| 4 | PC(4) | AM(4) | – |
| ⋮ | ⋮ | ⋮ | ⋮ |
| k | PC(k) | AM(k) | AM#(1) |
| ⋮ | ⋮ | ⋮ | ⋮ |
| n | PC(n) | AM(n) | – |

53 Pump Drive Circuit
54 Valve Drive Circuit
41 Operation Unit
100
112 Change Processing Unit
120 Specification Processing Unit
102 Drive Control Unit
103 Acquiring Unit
104 Pulse Wave Amplitude Extracting Unit
106 Blood Pressure Calculating Unit
108 Display Processing Unit
40 Display Unit
47 Body Movement Detection Unit
33 Oscillation Circuit
43 Flash Memory

BLOOD PRESSURE INFORMATION DISPLAY DEVICE, BLOOD PRESSURE INFORMATION DISPLAY SYSTEM, BLOOD PRESSURE INFORMATION DISPLAY METHOD, AND RECORDING MEDIUM RECORDED WITH BLOOD PRESSURE INFORMATION DISPLAY PROGRAM

This is a Continuation of International Patent Application No. PCT/TP2009/066258 filed Sep. 17, 2009, which claims priority to Japanese Patent Application No. 2008-259891 filed Oct. 6, 2008. The disclosures of the prior applications are hereby incorporated by reference herein in their entirety.

TECHNICAL FIELD

The present invention relates to blood pressure information display devices, blood pressure information display systems, blood pressure information display methods, and blood pressure information display programs, and in particular, to a blood pressure information display device, a blood pressure information display system, a blood pressure information display method, and a recording medium recorded with a blood pressure information display program for calculating a blood pressure value of a living body based on a pulse wave amplitude through an oscillometric method, and the like, and displaying the calculated blood pressure value as blood pressure information.

BACKGROUND ART

In the blood pressure measurement with the oscillometric method, the compressing pressure, that is, the cuff pressure of the cuff wrapped around a predetermined site (e.g., upper arm) of the living body is gradually changed in speed to extract the vibration component generated at the cuff in the process, that is, the amplitude of the cuff pulse wave (pressure pulse wave). The blood pressure is calculated based on the change of the extracted pulse wave amplitude with respect to the cuff pressure.

In a general electronic sphygmomanometer of the oscillometric method, pressure control as well as pulse wave signal analysis, blood pressure calculation, and blood pressure display are automatically carried out. While the cuff pulse wave is being measured, the pulse wave information not preferable in the calculation of the blood pressure sometimes get mixed as noise due to the movement (body motion) of the body, the vibration of the outer environment, and the physiological state such as irregular heart beat.

In the conventional electronic sphygmomanometer, devisal is made such as removing or correcting the unnecessary pulse wave information with a unique algorithm. However, when automatically detecting noise and automatically correcting the pulse wave amplitude, the noise may not be completely removed and may become an error, or an appropriate correction may not necessarily be performed. Furthermore, whether or not the noise is really removed cannot be recognized since the correction algorithm of the pulse wave amplitude is unknown to the user.

Patent document 1 (Japanese Unexamined Patent Publication No. 07-236617) proposes easily determining the appropriateness of the measurement state by displaying information on the corrected (smoothed) pulse wave amplitude. Patent document 2 (Japanese Unexamined Patent Publication No. 2002-272689) proposes making the determination on whether or not the reliable blood pressure value is obtained during the blood pressure measurement by displaying the normalized pulse wave amplitude in a graph during the blood pressure measurement.

Patent Document 1: Japanese Unexamined Patent Publication No. 07-236617

Patent Document 2: Japanese Unexamined Patent Publication No. 2002-272689

DISCLOSURE OF THE INVENTION

Problems to be Solved by the Invention

According to the invention of patent document 1 (Japanese Unexamined Patent Publication No. 07-236617), the user can grasp how much collected pulse wave amplitude has been corrected, but needs to conduct the measurement again if correction is not appropriately made since the correction algorithm itself cannot be changed.

According to the invention of patent document 2 (Japanese Unexamined Patent Publication No. 2002-272689) as well, remeasurement is required when determined that the reliable blood pressure value is not obtained.

In view of solving the above-described problems, it is an object of the present invention to provide a blood pressure information display device, a blood pressure information display system, a blood pressure information display method, and a recording medium recorded with a blood pressure information display program capable of enhancing the reliability of the blood pressure value presented as blood pressure information even with one measurement.

Means for Solving the Problem

In accordance with one aspect of the present invention, there is provided a blood pressure information display device for calculating a blood pressure value, and displaying the calculated blood pressure value as blood pressure information, the blood pressure information display device including: a display unit; an operation unit for accepting an operation by a user; a cuff to be wrapped around a predetermined measurement site of a person to be measured; an adjustment unit for adjusting an inner pressure of the cuff; a pressure detection unit for detecting a cuff pressure signal representing the pressure in the cuff; an acquiring unit for acquiring the cuff pressure signal in time-series from the pressure detection unit when a drive control of the adjustment unit is being carried out; an extracting unit for extracting a pulse wave amplitude for every beat based on the cuff pressure signal; a display processing unit for displaying pulse wave amplitude information representing a plurality of extracted pulse wave amplitudes on the display unit; a change processing unit for performing a process of changing a magnitude of a specified pulse wave amplitude of the plurality of extracted pulse wave amplitudes according to an instruction from the operation unit when a predetermined instruction is input from the operation unit; and a calculating unit for calculating a reference blood pressure value by applying a predetermined algorithm to a plurality of pulse wave amplitudes reflecting the change on the specified pulse wave amplitude; wherein the display processing unit displays the reference blood pressure value on the display unit as the blood pressure information.

Preferably, the blood pressure information display device further includes a storage unit for storing the plurality of extracted pulse wave amplitudes in association with at least one of a cuff pressure or a time, and for storing an amplitude value subsequent to the specified pulse wave amplitude is changed in association with a cuff pressure or a time at which the specified pulse wave amplitude is detected.

Preferably, the display processing unit displays the plurality of extracted pulse wave amplitudes along a cuff pressure axis or a time axis as the pulse wave amplitude information.

Preferably, the change processing unit changes a position of the specified pulse wave amplitude on the cuff pressure axis or the time axis according to the instruction from the operation unit.

Preferably, the change processing unit adds a pulse wave amplitude having a magnitude corresponding to an instruction to a specified position on the cuff pressure axis or the time axis according to the instruction from the operation unit.

Preferably, the change processing unit accepts the specification of change for only a predetermined number of pulse wave amplitudes.

Preferably, the change processing unit accepts an instruction to change only within a predetermined range of an original magnitude for the specified pulse wave amplitude.

Preferably, the display processing unit further notifies that the reference blood pressure value is a reference value in association with the reference blood pressure value.

Preferably, the calculating unit calculates an actual measurement blood pressure value by applying the predetermined algorithm to the plurality of extracted pulse wave amplitudes; and the display processing unit further displays the actual measurement blood pressure value along with the pulse wave amplitude information.

Preferably, the blood pressure information display device further includes: a specification processing unit for specifying at least one of the plurality of extracted pulse wave amplitudes as a changing candidate by detecting noise; wherein the display processing unit displays the specified pulse wave amplitude so as to be selectable.

Preferably, the blood pressure information display device further includes: a specification processing unit for specifying at least one of the plurality of extracted pulse wave amplitudes as a changing candidate by detecting noise; wherein the display processing unit displays the specified pulse wave amplitude as the changing candidate.

Preferably, the blood pressure information display device further includes: an authentication information detection unit for detecting authentication information for authenticating the user; wherein the change processing unit executes a changing process of the plurality of extracted pulse wave amplitudes only when user is authenticated based on the authentication information detected by the authentication information detection unit.

In accordance with another aspect of the present invention, there is provided a blood pressure information display system including a pulse wave measurement device and a blood pressure information display device; wherein the pulse wave measurement device includes, a cuff to be wrapped around a predetermined measurement site of a person to be measured, an adjustment unit for adjusting an inner pressure of the cuff, a pressure detection unit for detecting a cuff pressure signal representing the pressure in the cuff, and an acquiring unit for acquiring the cuff pressure signal in time-series from the pressure detection unit when a drive control of the adjustment unit is being carried out; the blood pressure information display device includes, a display unit, an operation unit for accepting an operation by a user, a display processing unit for displaying pulse wave amplitude information representing a plurality of pulse wave amplitudes extracted by the cuff pressure signal of time-series on the display unit, a change processing unit for performing a process of changing a magnitude of a specified pulse wave amplitude of the plurality of extracted pulse wave amplitudes according to an instruction from the operation unit when a predetermined instruction is input from the operation unit, and a calculating unit for calculating a reference blood pressure value by applying a predetermined algorithm to a plurality of pulse wave amplitudes reflecting the change on the specified pulse wave amplitude; and the display processing unit displays the reference blood pressure value on the display unit as the blood pressure information.

In accordance with still another aspect of the present invention, there is provided a blood pressure information display method for calculating a blood pressure value, and displaying the calculated blood pressure value as blood pressure information, the method including the steps of: displaying pulse wave amplitude information representing a plurality of pulse wave amplitudes extracted from a pulse wave measured in a process of gradually changing a cuff pressure; changing a magnitude of a specified pulse wave amplitude of the plurality of extracted pulse wave amplitudes according to an instruction from a user when a predetermined instruction is input: calculating a reference blood pressure value by applying a predetermined algorithm to the plurality of pulse wave amplitudes subsequent to the change; and displaying the reference blood pressure value as the blood pressure information.

In accordance with further another aspect of the present invention, there is provided a recording medium recorded with a blood pressure information display program for calculating a blood pressure value, and displaying the calculated blood pressure value as blood pressure information, the program causing a computer to execute the steps of: displaying pulse wave amplitude information representing a plurality of pulse wave amplitudes extracted from a pulse wave measured in a process of gradually changing a cuff pressure; changing a magnitude of a specified pulse wave amplitude of the plurality of extracted pulse wave amplitudes according to an instruction from a user when a predetermined instruction is input: calculating a reference blood pressure value by applying a predetermined algorithm to the plurality of pulse wave amplitudes subsequent to the change; and displaying the reference blood pressure value as the blood pressure information.

Effect of the Invention

According to the present invention, the magnitude of the specified pulse wave amplitude of a plurality of extracted pulse wave amplitudes can be changed according to the operation of the user (medical staff). Therefore, a highly reliable blood pressure value can be presented even with one measurement.

BEST MODE FOR CARRYING OUT THE INVENTION

Figure 1:
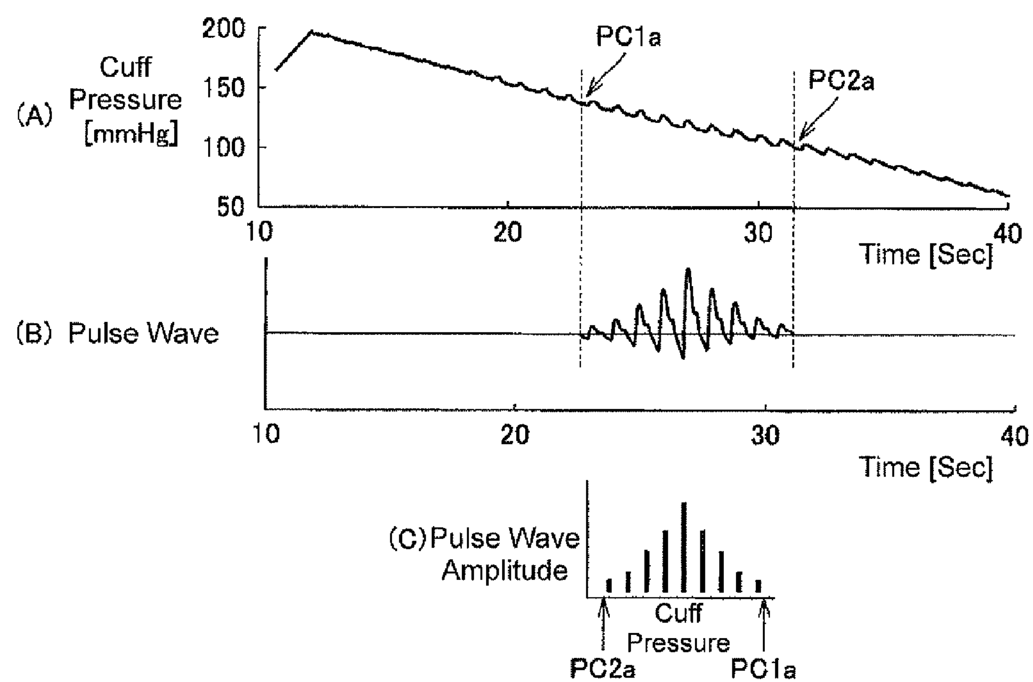
FIGS. 1A to 1C are views showing a typical example of a pulse wave amplitude obtained in the process of gradually depressurizing the cuff pressure.

Embodiments of the present invention will be described in detail with reference to the drawings. The same reference numerals are denoted from the same or corresponding portions in the figures, and the description thereof will not be repeated.

Figure 2:
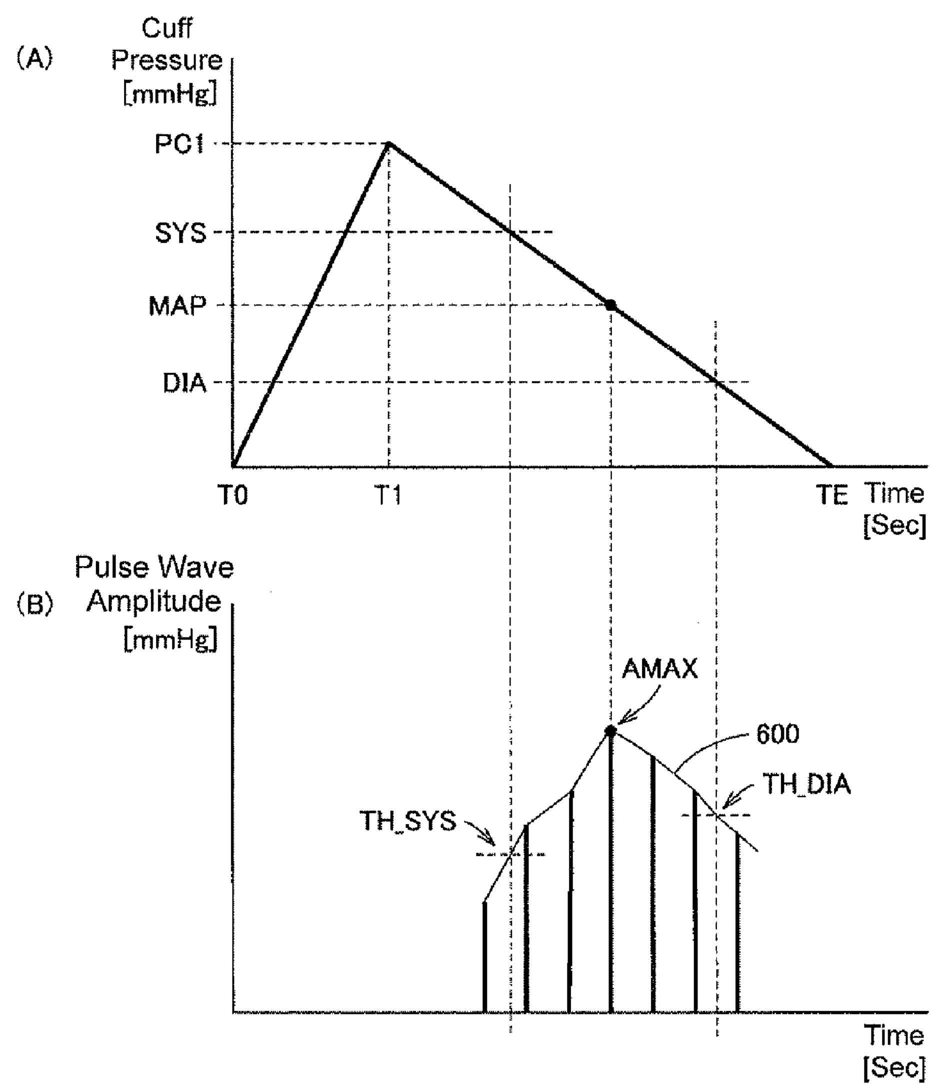
FIGS. 2A and 2B are views describing the blood pressure calculation method by the oscillometric method.
Figure 3:
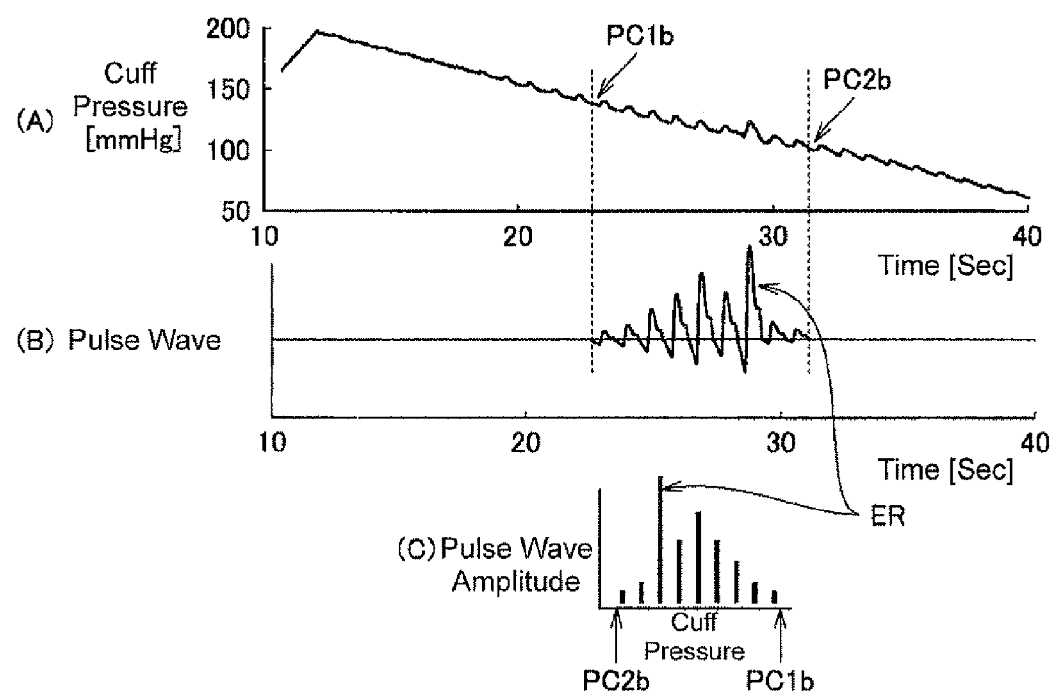
FIGS. 3A to 3C are views showing an example of the pulse wave amplitude when noise is mixed to the pulse wave.

The blood pressure information display device according to the present embodiment calculates the blood pressure value (systolic blood pressure and diastolic blood pressure) through the oscillometric method, and displays the calculated blood pressure value as blood pressure information. First, the blood pressure calculation method by the oscillometric method will be briefly described using FIG. 1 to FIG. 3. In the present embodiment, the method of calculating the blood pressure is assumed as the oscillometric method, but this is not the sole case, and the method merely needs to be a method of calculating the blood pressure value based on the pulse wave amplitude.

FIGS. 1A and 1B are views showing a typical example of a pulse wave amplitude obtained in the process of gradually depressurizing the cuff pressure. FIG. 1A shows the signal of the detected cuff pressure (unit: mmHg) along a time axis. FIG. 1B shows the pulse wave component after the filtering process along the same time axis as the graph of FIG. 1A. FIG. 1C shows the amplitude value of the pulse wave component for each beat shown in FIG. 1B along a cuff pressure axis. The cuff pressure PC1*a* shown on the cuff pressure axis of FIGS. 1A and 1C is the pressure value at the time point the pulse wave starts to be detected, and the cuff pressure PC2*a* is the pressure value at the time point the pulse wave is no longer detected.

The bleeding arrests when the inner pressure of the cuff becomes higher than the systolic blood pressure, and the blood flow resumes when the pressure is gradually released. The oscillometric method uses the characteristics that the pulse wave amplitude changes as shown in FIG. 1C in the process.

FIGS. 2A and 2B are views for describing the blood pressure calculation method by the oscillometric method. FIG. 2A shows the cuff pressure (unit: mmHg) that gradually changes along the time axis, and FIG. 2B partially shows the pulse wave amplitude (unit: mmHg) that superimposes on the cuff pressure along the same time axis.

With reference to FIG. 2A, the cuff pressure is pressurized to higher than or equal to the systolic blood pressure ("PC1" in the figure) of the person to be measured and then depressurized at a constant speed. A predetermined algorithm is applied to the pulse wave amplitude superimposing on the detected cuff pressure at the gradually depressurizing stage to calculate the systolic blood pressure and the diastolic blood pressure. With reference to FIG. 2B, the cuff pressure corresponding to a point AMAX, at which the pulse wave amplitude becomes a maximum during the depressurization of the cuff pressure, is found to be the average blood pressure ("MAP" in the figure) in the oscillometric method. When the maximum point of the pulse wave amplitude is detected, a value obtained by multiplying a predetermined constant (e.g., 0.5) to the maximum point AMAX is assumed as the threshold value TH_SYS, and a value obtained by multiplying a predetermined constant (e.g., 0.7) to the maximum point AMAX is assumed as the threshold value TH_DIA. The cuff pressure higher than the average blood pressure (MAP) corresponding to the point where an envelope curve 600 of the pulse wave amplitude and the threshold value TH_SYS intersects is determined as the systolic blood pressure ("SYS" in the figure). The cuff pressure lower than the average blood pressure (MAP) corresponding to the point where the envelope curve 600 of the pulse wave amplitude and the threshold value TH_DIA intersects is determined as the diastolic blood pressure ("DIA" in the figure).

As apparent from the figure, the shape of the envelope curve of the pulse wave amplitude influences the accuracy of the blood pressure value calculation according to the oscillometric method. In FIGS. 2A and 2B, the depressurization measurement method (method of calculating the blood pressure based on the pulse wave measured during depressurization) has been described by way of example, but similar aspects also apply to the pressurization measurement method.

FIGS. 3A to 3C are views showing an example of the pulse wave amplitude when noise is mixed to the pulse wave. The graphs of FIGS. 3A, 3B, and 3C respectively correspond to FIGS. 1A, 1B, and 1C. In FIG. 3C, a pulse wave amplitude ER that has an apparently abnormal value out of a plurality of pulse wave amplitudes exits. If the blood pressure is calculated based on such plurality of pulse wave amplitudes, the cuff pressure at the time point the amplitude ER is detected is determined as the average blood pressure, and hence a non-accurate blood pressure value will be calculated. Even with the sphygmomanometer loaded with a correction algorithm for automatically detecting noise and removing the detected noise, most sphygmomanometers do not know what processes are being carried out inside. Even if the processes are known, a wrong correction process may be carried out on the part of the medical staffs, in which case measurement again needs to be carried out.

The existence of the abnormal pulse wave amplitude ER shown in FIG. 3C can be easily found by medical staffs such as doctors. The medical staff can also decide what the size (or the position) of the abnormal pulse wave amplitude ER is to be through experience. The blood pressure information display device according to the present embodiment enables the size of the pulse wave amplitude to be manually changed assuming that the operation is carried out by the medical staff. The measurement success rate, and the reliability of the blood pressure value thus can be enhanced.

The blood pressure information display device according to each embodiment will now be described in detail below. The blood pressure information display device is assumed to be handled by the medical staff having sufficient knowledge of blood pressure. Therefore, the blood pressure information display device is the blood pressure information display device for hospitals, and is representatively assumed to be installed in the examination room and the like in the hospital. In the present embodiment, the blood pressure information display device at least calculates the blood pressure value (systolic blood pressure and diastolic blood pressure) based on the pulse wave amplitude through the oscillometric method, and the like, and displays the calculation result as the blood pressure information.

In the present embodiment, the "medical staff" includes at least doctors, nurses, clinical laboratory technicians, and pharmacists, and may also include assistants who assist the operation by receiving instructions from doctors, and the like.

First Embodiment

Regarding Outer Appearance and Configuration

First, the outer appearance and the configuration of the blood pressure information display device according to a first embodiment of the present invention will be described.

(Regarding Outer Appearance)

Figure 4:
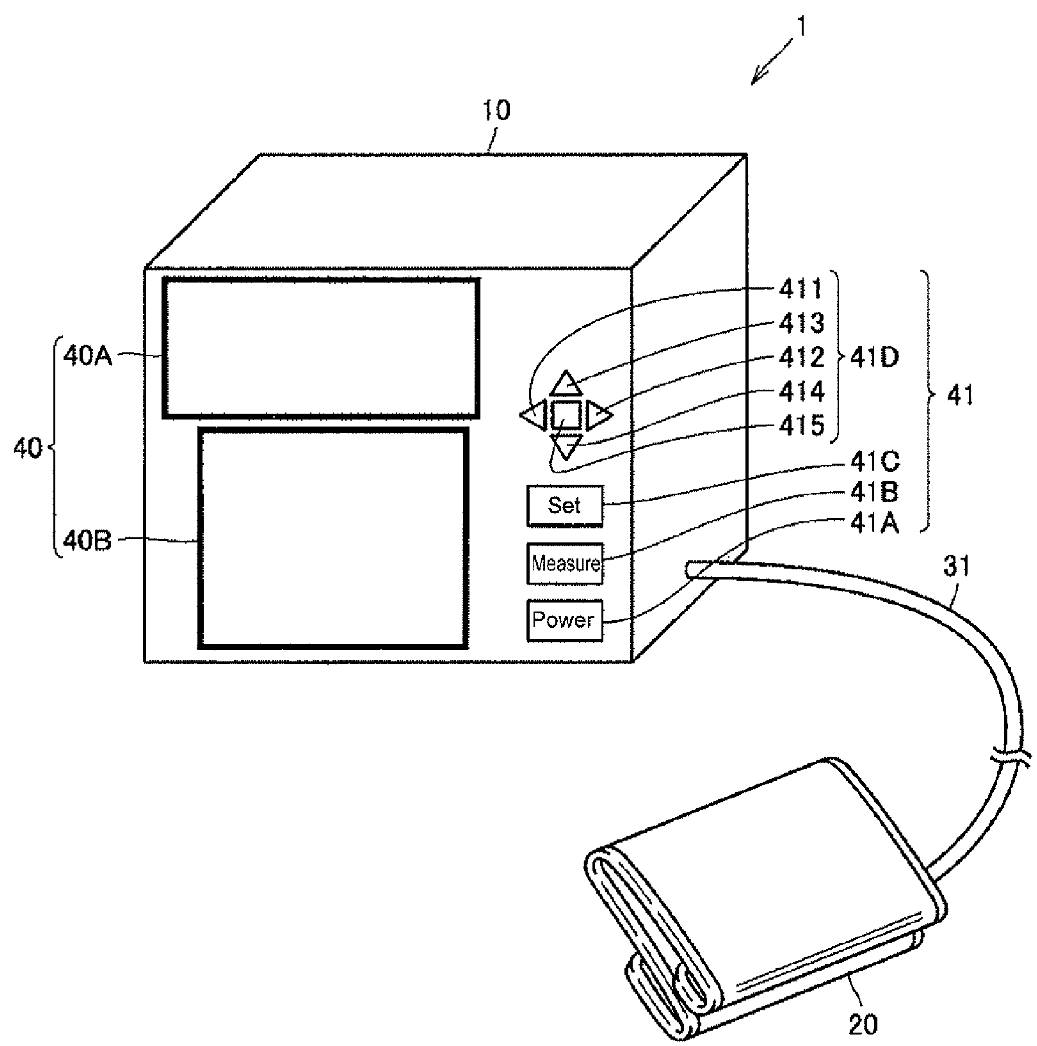
FIG. 4 is a perspective view of an outer appearance of a blood pressure information display device according to a first embodiment of the present invention.

FIG. 4 is a perspective view of an outer appearance of a blood pressure information display device 1 according to a first embodiment of the present invention. The blood pressure information display device 1 has a function of measuring a pulse wave.

With reference to FIG. 4, the blood pressure information display device 1 includes a main body 10, a cuff 20 that can be wrapped around a predetermined measuring site (e.g., upper arm) of the person to be measured, and an air tube 31 for connecting the main body 10 and the cuff 20. A display unit 40 configured by liquid crystal, and the like, and an operation unit 41 for receiving instructions from the user (representatively doctor) are arranged on the surface of the main body 10.

The display unit 40 includes a first display region 40A for displaying the blood pressure measurement result as a numerical value, and a second display region 40B for displaying the pulse wave amplitude information.

The operation unit 41 includes a power switch 41A for receiving the input of instruction to turn ON or OFF the power, a measurement switch 41B for receiving the instruction to start the measurement, a set switch 41C for receiving the instruction for various types of setting processes and readout of stored values, and a cursor switch 41D. The cursor switch 41D includes a leftward switch 411, a rightward switch 412, an upward switch 413, a downward switch 414, and a determination switch 415.

The main body 10 of the blood pressure information display device 1 is mounted on a desk or a dedicated stand in the examination room.

(Regarding Hardware Configuration)

Figure 5:
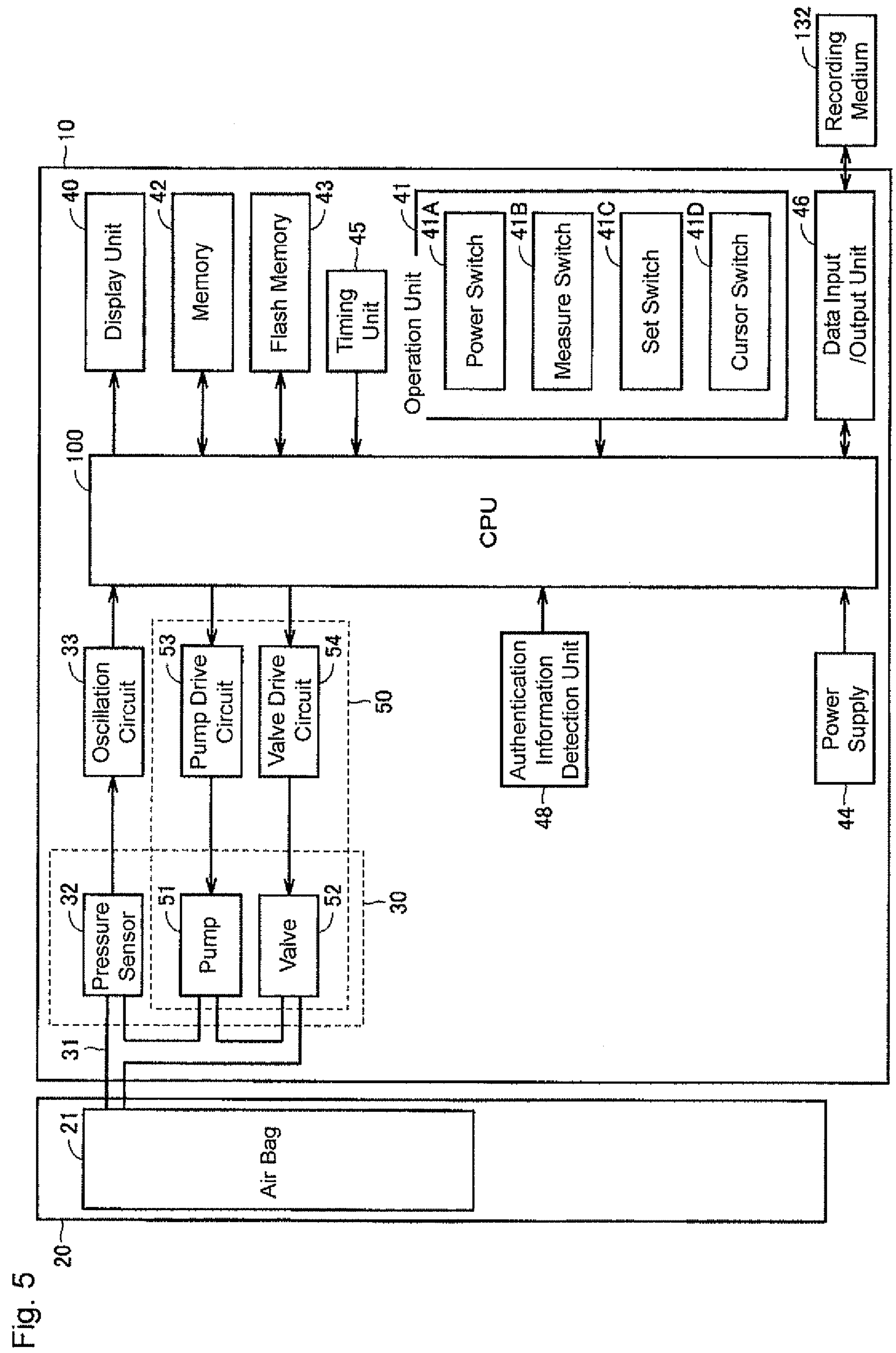
FIG. 5 is a block diagram showing a hardware configuration of the blood pressure information display device according to the first embodiment of the present invention.

FIG. 5 is a block diagram showing a hardware configuration of the blood pressure information display device 1 according to the first embodiment of the present invention.

With reference to FIG. 5, the cuff 20 of the blood pressure information display device 1 includes an air bag 21. The air bag 21 is connected to an air system 30 through the air tube 31.

In addition to the display unit 40 and the operation unit 41, the main body 10 includes the air system 30, a CPU (Central Processing Unit) 100 for controlling each unit in a concentrated manner and for carrying out various calculation processes, a memory 42 for storing programs for causing the CPU 100 to perform a predetermined operation and various data, a non-volatile memory (e.g., flash memory) 43 for storing the measured blood pressure, a power supply 44 for supplying power to the CPU 100, a timing unit 45 for performing the timing operation, and a data input/output unit 46 for receiving the input of data from the outside.

The air system 30 includes a pressure sensor 32 for detecting the pressure (cuff pressure) in the air bag 21, a pump 51 for supplying air to the air bag 21 to pressurize the cuff pressure, and a valve 52 that opens and closes to exhaust or enclose the air of the air bag 21.

The main body 10 also includes an oscillation circuit 33, a pump drive circuit 53, and a valve drive circuit 54 in association with the air system 30.

The pressure sensor 32 is a capacitance type pressure sensor, where the capacitance value changes according to the cuff pressure. The oscillation circuit 33 outputs a signal of an oscillating frequency corresponding to the capacitance value of the pressure sensor 32 to the CPU 100. The CPU 100 converts the signal obtained from the oscillation circuit 33 to pressure, and detects the pressure. The pump drive circuit 53 controls the drive of the pump 51 based on a control signal provided from the CPU 100. The valve drive circuit 54 performs the open/close control of the valve 52 based on a control signal provided from the CPU 100.

The pump 51, the valve 52, the pump drive circuit 53, and the valve drive circuit 54 configure an adjustment unit 50 for adjusting the cuff pressure. It should be recognized that the device for adjusting the cuff pressure is not limited thereto.

The data input/output unit 46 performs readout and write of programs and data with respect to a removable recording medium 132. Alternatively, the data input/output unit 46 may transmit and receive programs and data through a communication line with respect to an external computer (not shown).

Although the cuff 20 includes the air bag 21, the fluid supplied to the cuff 20 is not limited to air and may be liquid or gel. Alternatively, the fluid is not the sole case, and may be uniform fine particles such as micro-beads.

(Regarding Function Configuration)

Figure 6:
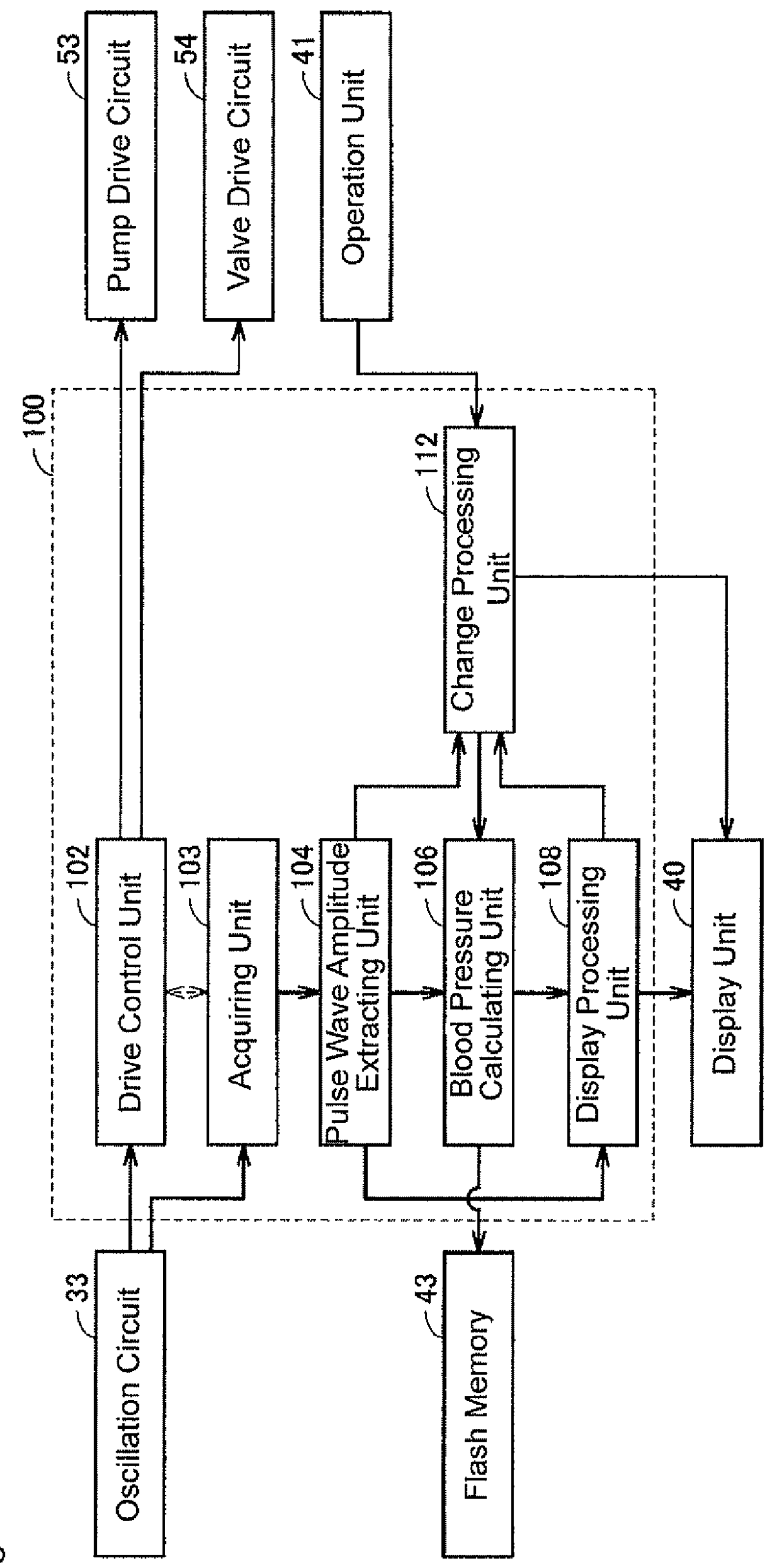
FIG. 6 is a block diagram showing a function configuration of the blood pressure information display device according to the first embodiment of the present invention.

FIG. 6 is a block diagram showing a function configuration of the blood pressure information display device 1 according to the first embodiment of the present invention. FIG. 6 only shows the peripheral hardware that directly exchanges signals with each unit of the CPU 100 for the sake of simplifying the explanation.

The CPU 100 includes a drive control unit 102, an acquiring unit 103, a pulse wave amplitude extracting unit 104, a blood pressure calculating unit 106, a display processing unit 108, and a change processing unit 112.

The drive control unit 102 controls the drive of the pump drive circuit 53 and the valve drive circuit 54 based on the signal from the oscillation circuit 33 to gradually change the pressure in the cuff 20. In the depressurization measurement method, the cuff pressure is raised up to a specific pressure value (higher than or equal to systolic blood pressure) at high speed, and then the cuff pressure is depressurized at a constant speed or in a step-wise manner after reaching the specific pressure value. In the case of the pressurization measurement method, the cuff pressure is pressurized at a constant speed or in a step-wise manner until reaching a specific pressure value.

The acquiring unit 103 acquires the cuff pressure signal in time-series based on the output from the oscillation circuit 33 when the drive control at gradual speed up by the drive control unit 102 is being carried out. The vibration component, that is, the cuff pulse wave (pressure pulse wave) generated at the cuff 20 is thereby measured.

The pulse wave amplitude extracting unit 104 extracts the pulse wave amplitude for one beat based on the cuff pressure signal, that is, the cuff pulse wave acquired in time-series by the acquiring unit 103.

The blood pressure calculating unit 106 calculates the blood pressure value (systolic blood pressure and diastolic blood pressure) of the person to be measured according to the oscillometric method. The blood pressure calculating unit 106 calculates a first blood pressure value based on a plurality of extracted (non-processed) pulse wave amplitudes and a predetermined algorithm. The blood pressure calculating unit 106 also calculates a second blood pressure value based on a plurality of pulse wave amplitudes reflecting the change by the change processing unit 112, to be described later, and the algorithm. The algorithm for blood pressure calculation does not include the correction algorithm such as smoothening of the pulse wave amplitude.

The first blood pressure value and/or the second blood pressure value calculated by the blood pressure calculating unit 106 may be stored in the flash memory 43.

The display processing unit 108 performs a process of displaying the first blood pressure value and the second blood pressure value calculated in the blood pressure calculating unit 106. The display processing unit 108 also displays first pulse wave amplitude information representing a plurality of pulse wave amplitudes extracted by the pulse wave amplitude extracting unit 104 when displaying the first blood pressure value. The display processing unit 108 also displays second pulse wave amplitude information representing a plurality of pulse wave amplitudes reflecting the change by the change processing unit 112 when displaying the second blood pressure value.

The display processing unit 108 preferably performs the display of notifying that the second blood pressure value is merely a reference value when displaying the second blood pressure value. In this regards, the second blood pressure value is considered as “reference blood pressure value”. The first blood pressure value, on the other hand, is considered as “actual measurement blood pressure value” since it is a value calculated based on actual measurement data.

The actual measurement blood pressure value and the first pulse wave amplitude information are displayed together herein, but only one of which may be displayed first when presenting the actual measurement result. When displaying only the actual measurement blood pressure value first, the first pulse wave amplitude information is displayed when an instruction to process is input through the operation unit 41.

When the instruction to process is input through the operation unit 41 after the actual measurement result is displayed, the change processing unit 112 performs a process of changing the magnitude of the specified pulse wave amplitude of a plurality of extracted pulse wave amplitudes in response to the instruction from the operation unit 41. A specific process of the change processing unit 112 will be described later.

The operation of each function block described above may be realized by executing a software stored in the memory 42, or at least one may be realized with hardware.

<Regarding Operation>

Figure 7:
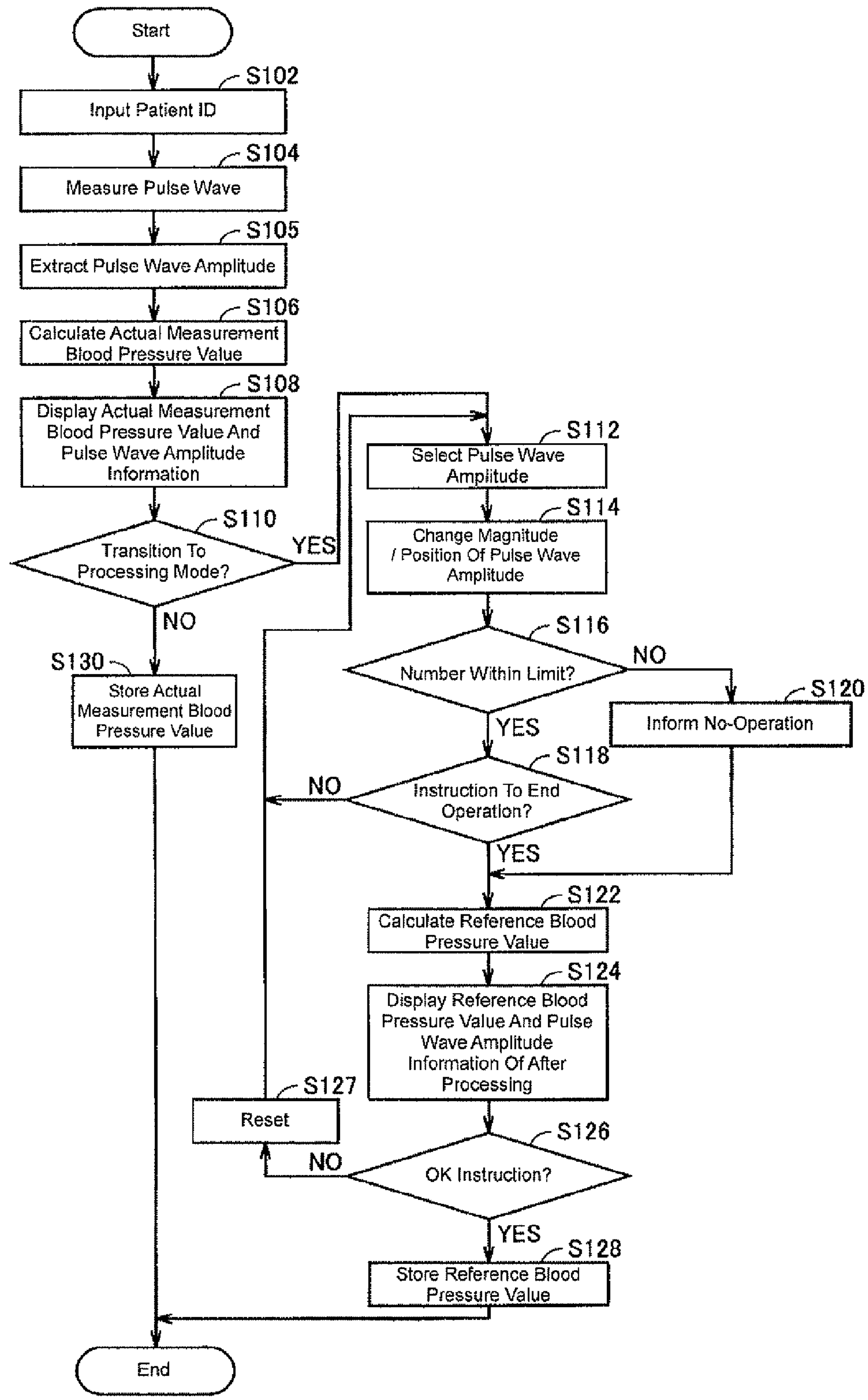
FIG. 7 is a flowchart of the measurement and display process (pulse wave measurement and blood pressure information display process) in the first embodiment of the present invention.

FIG. 7 is a flowchart of the pulse wave measurement and the blood pressure information display process (hereinafter referred to as “measurement and display process”) according to the first embodiment of the present invention. The process shown in the flowchart of FIG. 7 is stored in the memory 42 in advance as a program, where the function of the measurement and display process is realized when the CPU 100 reads out and executes the program. The following process is assumed to start when the pushing of the power switch 41A is detected. The operation of the operation unit 41 including the power switch 41A is assumed to be performed by a medical staff. Therefore, the subsequent process may be started only when a predetermined operation (e.g., simultaneous pushing of a plurality of switches, etc.) is performed after the pushing of the power switch 41A. Alternatively, the blood pressure information display device 1 may include an authentication information detection unit 48 (see FIG. 5) for detecting the authentication information of the user. In such a case, the CPU 100 may start the subsequent process only when determined that the authentication information detected by the authentication information detection unit 48 and the authentication information stored in the memory 42 etc. in advance match with each other. The authentication information may be a fingerprint, or information recorded on an ID card.

With reference to FIG. 7, the CPU 100 first receives the input of a patient ID based on a signal from the operation unit 41 (step S102).

When the measurement switch 41B is pushed thereafter, the pulse wave measurement process is executed through a known method (step S104). Specifically, the drive control unit 102 performs the control of gradually changing the cuff pressure, and the acquiring unit 103 acquires the cuff pressure signal in time-series in parallel to the drive control. More specifically, the acquiring unit 103 acquires the cuff pressure signal at a predetermined sampling cycle from the oscillation circuit 33, and records the same in a predetermined region of the memory 42. In the memory 42, the cuff pressure data is stored in association with time data representing the acquired time.

After the measurement of the pulse wave is finished, the pulse wave amplitude extracting unit 104 extracts the pulse wave amplitude for each beat based on the cuff pressure signal of time-series recorded in the memory 42 through a known method (step S105). Specifically, the pulse wave waveform shown in FIG. 1B is extracted by filter processing the cuff pressure signal shown in FIG. 1A. The pulse wave amplitude for each beat shown in FIG. 1C is then extracted based on the extracted pulse wave waveform. The value of each extracted pulse wave amplitude is stored in a predetermined region of the memory 42 in association with the cuff pressure value or the time.

Figure 8:
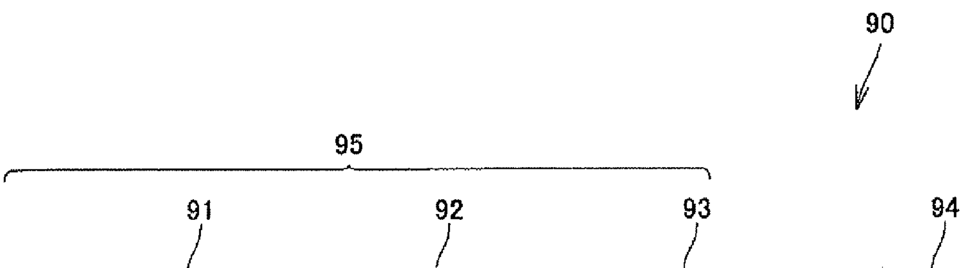
FIG. 8 is a view showing one example of a data structure of the pulse wave related information stored in the memory.

FIG. 8 is a view showing one example of a data structure of the pulse wave related information 90 stored in the memory 42.

With reference to FIG. 8, the pulse wave related information 90 includes four items, that is, item 91 indicating time data, item 92 indicating cuff pressure data, item 93 indicating extracted pulse wave amplitude (also referred to as “actual measurement amplitude”) data, and item 94 indicating pulse wave amplitude after change (also referred to as “processed amplitude") data. The information consisting of items 91 to 93 is also referred to as actual measurement information 95.

The cuff pressure data is stored in association with the time data, and the actual measurement amplitude data and the processed amplitude data are stored in association with the time data or the cuff pressure data. A numerical value including "0" is assumed to be recorded in the actual measurement amplitude data AM(1), . . . , AM(n). "NULL" is assumed to be recorded in the item 94 of processed amplitude data until transitioning to the processing mode.

The blood pressure calculating unit 106 then applies a predetermined algorithm on the pulse wave amplitude extracted in step S105, and calculates the systolic blood pressure and the diastolic blood pressure as the actual measurement blood pressure value (step S106). The blood pressure calculating unit 106 may further calculate the number of pulses through a known method.

The display processing unit 108 displays the actual measurement blood pressure value calculated in step S106 on the display unit 40 along with the first pulse wave amplitude information representing the plurality of pulse wave amplitudes extracted in step S105 (step S108). Specifically, the display processing unit 108 reads out the cuff pressure data and the actual measurement amplitude data in the pulse wave related information stored in the memory 42, and performs a display corresponding to such correspondence relationship. The display example is shown in FIGS. 9A and 9B.

Figure 9:
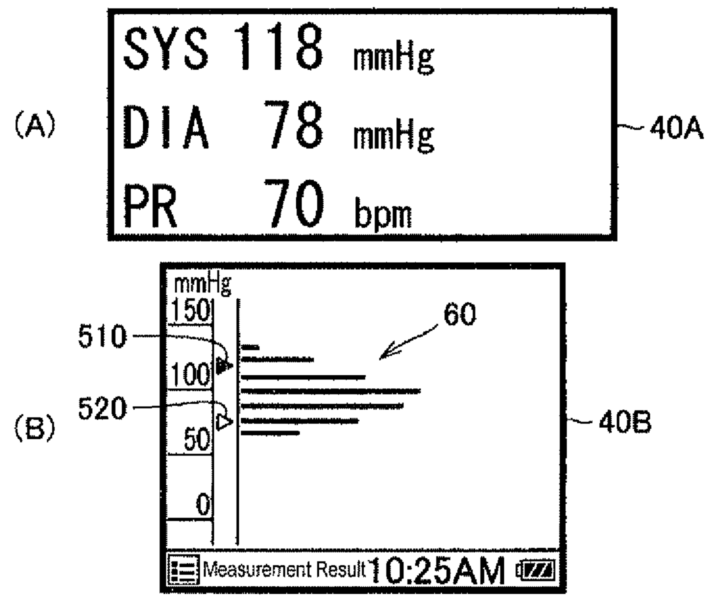
FIGS. 9A and 9B are views showing one example of a screen displayed in step S108 of FIG. 7.

With reference to FIG. 9A, the systolic blood pressure (SYS), the diastolic blood pressure (DIA), and the number of pulses (PR) are displayed in the first display region 40A of the display unit 40 as numerical values. With reference to FIG. 9B, the first pulse wave amplitude information 60 is displayed in the second display region 40B as a bar graph. In such graph, the vertical axis shows the cuff pressure and the horizontal axis shows the magnitude of the pulse wave amplitude. More specifically, a plurality of bars (hereinafter referred to as "amplitude bar") representing the magnitude of each pulse wave amplitude for a plurality of beats is displayed along the cuff pressure axis.

Therefore, since the magnitude of the pulse wave amplitude is displayed along the cuff pressure axis, whether or not the pulse wave amplitude of an abnormal magnitude (i.e., pulse wave amplitude mixed with noise) exists can be intuitively grasped by the medical staff. As shown in FIG. 9B, a mark 510 indicating the systolic blood pressure and a mark 520 indicating a diastolic blood pressure may be displayed on the cuff pressure axis.

In the present embodiment, the pulse wave amplitude for a plurality of beats is shown along the cuff pressure axis, but may be shown along the time axis.

Figure 10:
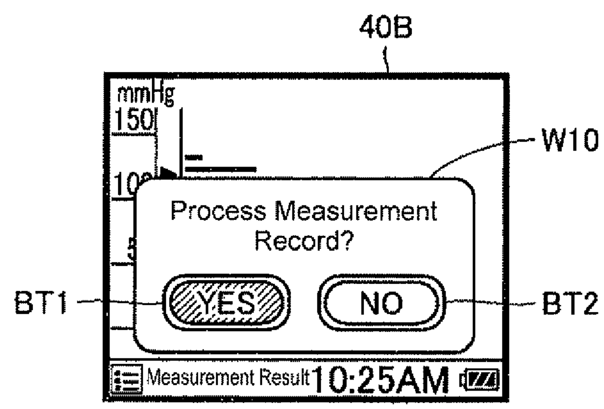
FIG. 10 is a view showing one example of a screen displayed in step S110 of FIG. 7.

Referring again to FIG. 7, the CPU 100 determines whether or not a predetermined instruction is input through the operation unit 41 when or after the actual measurement value calculation result is displayed in step S108 (step S110). That is, whether or not the instruction to transition to the processing mode is input is determined. FIG. 10 is a view showing one example of a screen displayed in step S110 of FIG. 7.

With reference to FIG. 10, a window W10 is displayed in the second display region 40B. The window W10 includes a message "process measurement record?", a button BT1 for receiving the instruction to process, and a button BT2 for instructing to terminate without processing.

When the instruction to transition to the processing mode is input, that is, when the button BT1 is instructed (YES in step S110), the process proceeds to step S112, and the pulse wave information changing process is executed. When the instruction to transition to the processing mode is not input, that is, when the button BT2 is instructed (NO in step S110), the process proceeds to step S130.

In step S130, the CPU 100 stores the actual measurement blood pressure value calculated in step S106 in the corresponding measurement result region of the flash memory 43.

Figure 11:
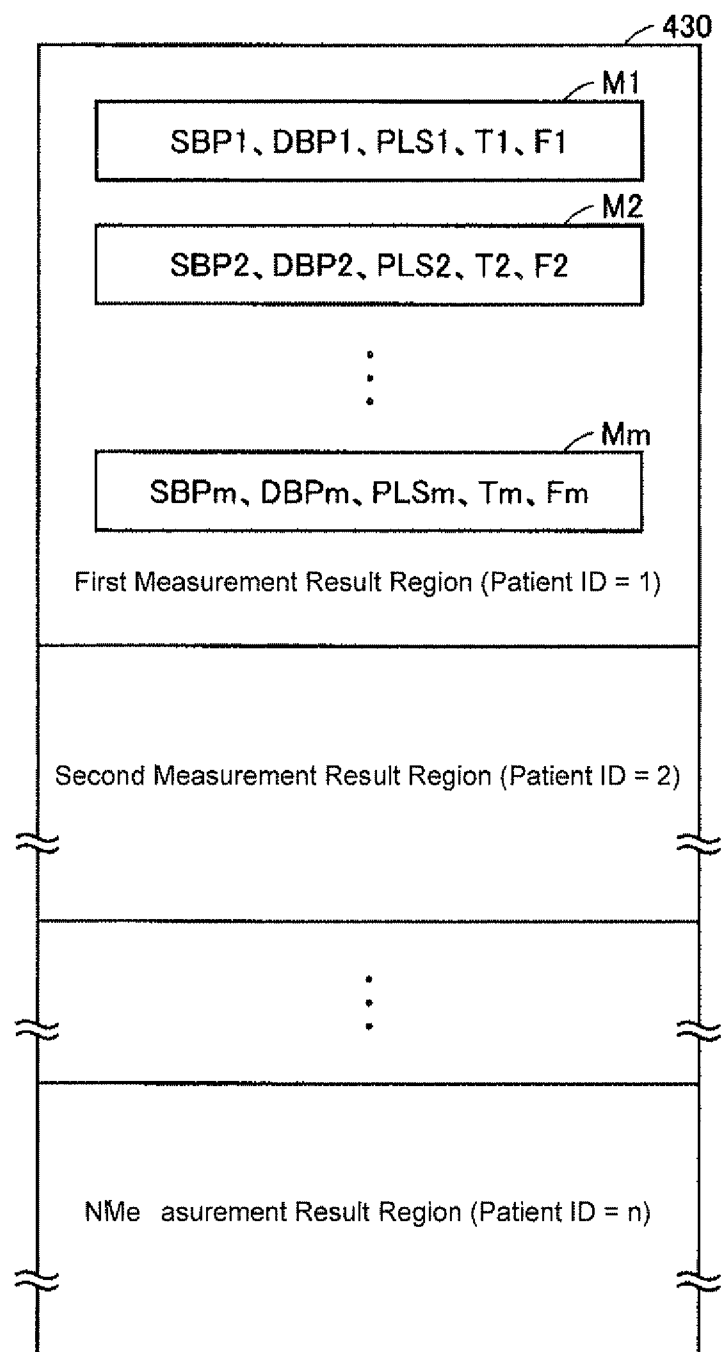
FIG. 11 is a view showing one example of a data structure of the flash memory.

FIG. 11 is a view showing one example of a data structure of the flash memory 43.

With reference to FIG. 11, the flash memory 43 includes a measurement result region for every patient ID. Each measurement result region stores a record in which the blood pressure value and the measurement date and time are associated with each other as blood pressure measurement data M1 to Mm (m=1, 2, 3, . . . ). Each blood pressure measurement data includes systolic blood pressure data SBP indicating the systolic blood pressure, diastolic blood pressure data DBP indicating the diastolic blood pressure, number of pulse data PLS indicating the number of pulse, measurement date and time data T, and identification flag F for identifying whether the measurement value is the actual measurement value or the reference value. The identification flag F stores, for example, "0" if the blood pressure value is an actual measurement value, and "1" if the blood pressure value is a reference value.

In step S130, the blood pressure measurement data is stored in the measurement result storage region corresponding to the patient ID input in step S102. Since the actual measurement blood pressure value is stored as the blood pressure measurement data herein, the value of the identification flag F is "0". Both the actual measurement value and the reference value may be stored in each blood pressure measurement data. In this case, the identification flag F is not necessary.

The blood pressure value, the measurement date and time, and the identification flag merely need to be stored in association with each other, and the form of storing using the record is not the sole case.

Therefore, if the blood pressure measurement result is recorded with the identification information indicating whether the relevant value is the actual measurement value or the reference value, whether or not the displayed value is a processed value can be recognized when subsequently reading out and displaying the blood pressure measurement result of the patient.

Figure 12:
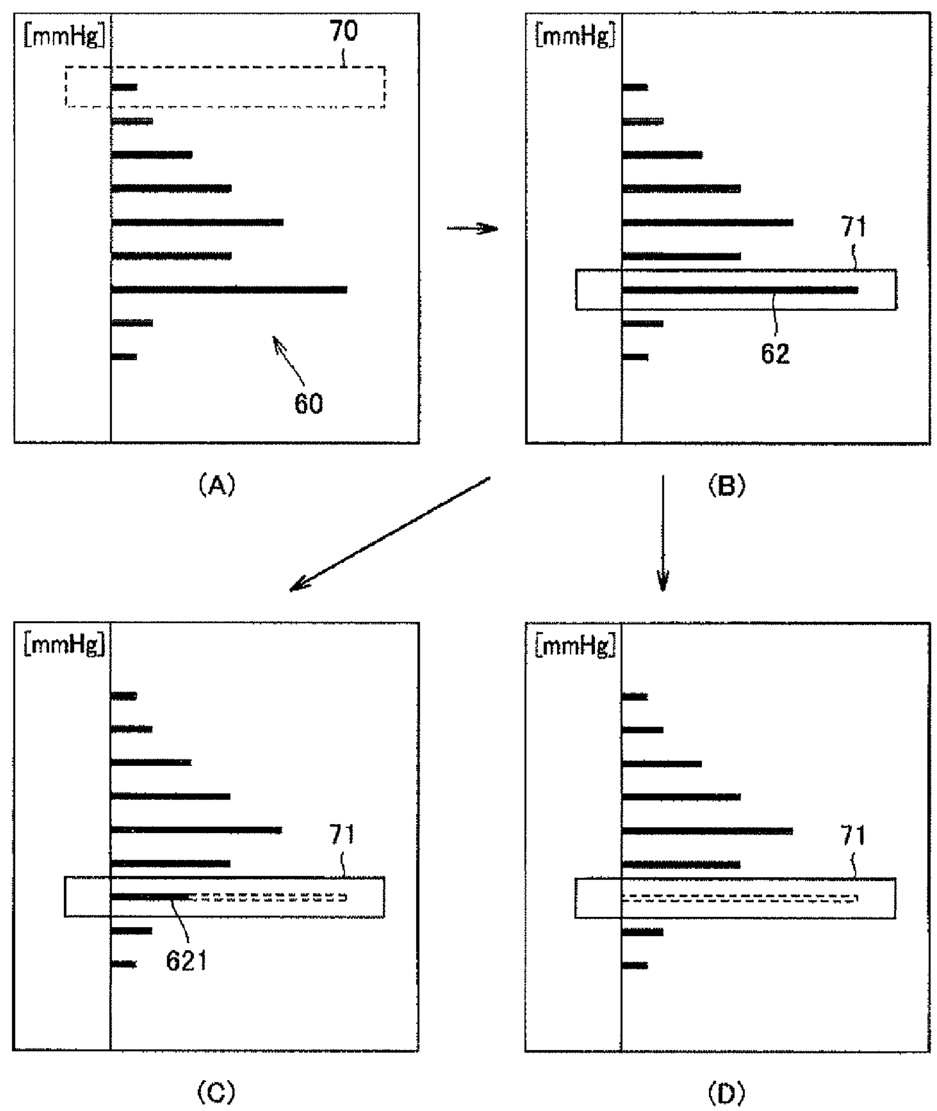
FIGS. 12A to 12D are views showing examples in which the magnitude of the pulse wave amplitude is changed.
Figure 13:
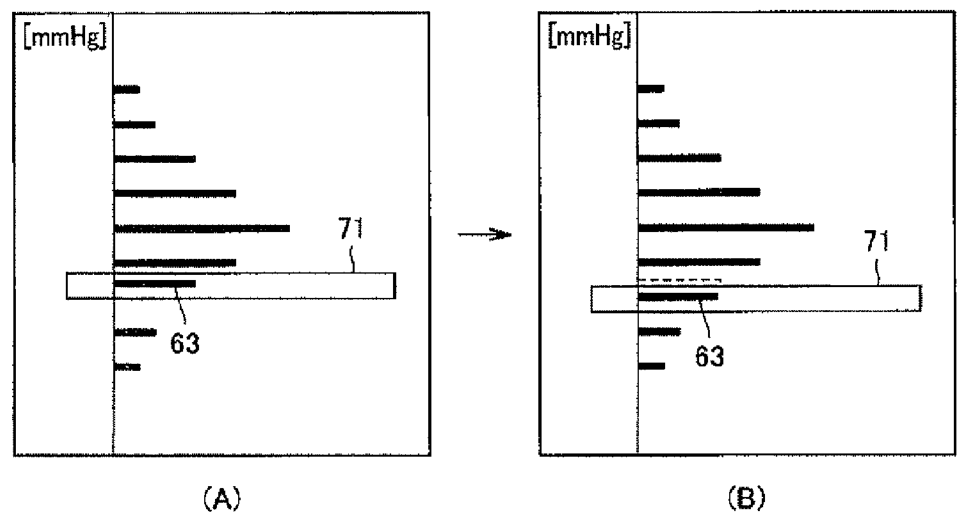
FIGS. 13A and 13B are views showing an example in which the appearance position of the pulse wave amplitude is changed.

The pulse wave information changing process (step S112 to step S120) will now be described below with reference to FIG. 12 and FIG. 13. FIGS. 12A to 12D are views showing an example in which the magnitude of the pulse wave amplitude is changed. A screen as shown in FIG. 12A is assumed to be displayed in the second display region 40B immediately after the instruction to transition to the processing mode is input in step S110. In FIG. 12A, the uppermost amplitude bar (pulse wave amplitude when the cuff pressure is the highest) is surrounded with a broken line frame 70. The broken line frame 70 functions as a movable cursor.

In step S112, the change processing unit 112 selects one pulse wave amplitude based on an instruction signal from the operation unit 41. That is, the specification (selection) of the amplitude bar to be changed of a plurality of amplitude bars displayed in the graph is accepted. More specifically, when decided by the medical staff that the uppermost amplitude bar surrounded with the broken line frame 70 is not the changing target, the downward switch 414 of the cursor switch 41D is operated to move the broken line frame 70 to the amplitude bar 62 to be changed. Thereafter, the determination switch 415 is pushed, so that the amplitude bar 62 surrounded with a solid line frame 71 is determined as the changing target as shown in FIG. 12B.

After the changing target is determined, the change processing unit 112 accepts change in the magnitude of the selected pulse wave amplitude (step S114). That is, change in the length of the amplitude bar 62 is accepted. The length of the amplitude bar 62 is changed based on the operation signals from the leftward and rightward switches 411, 412 of the cursor switch 41D. The change in the length of the amplitude bar 62 includes shortening, extending, and deleting. FIG. 12C shows an example in which the amplitude bar 62 is changed to an amplitude bar 621 with the original length shorted to about ⅓, and FIG. 12D shows an example in which the amplitude bar 62 is deleted.

When accepting the change in the length of the amplitude bar 62, the change processing unit 112 records the numerical value (AM#(1)) after the change in the field of the same row as the actual measurement amplitude data AM(k) representing the amplitude bar 62 of the item 94 of the processed amplitude data of the pulse wave related information 90 of the memory 42. For instance, if the amplitude bar 62 is deleted as in FIG. 12D, the processed amplitude data AM#(1) becomes "0".

The change in the magnitude of the pulse wave amplitude may not be the only one accepted, and the change in the position of the pulse wave amplitude may also be accepted. FIGS. 13A and 13B are views showing an example in which the amplitude bar 63 is moved either up or down along the cuff pressure axis. In the case of the person to be measured who has irregular heartbeat, the appearance timing of the pulse wave amplitude may shift from normal as shown in FIG. 13A. Therefore, the selection of the amplitude bar 63 showing the pulse wave amplitude detected at an abnormal position may be accepted and moved with the upward and downward switches 413, 414. FIG. 13B shows an example in which the amplitude bar 63 is moved to a normal position.

With reference again to FIG. 7, after the determination switch 415 of the cursor switch 41D is pushed to determine on the length of the selected amplitude bar, the change processing unit 112 determines whether or not the number of changed pulse wave amplitudes (amplitude bars) is within a limit (less than predetermined number) (step S116). When determined that the number of changed pulse wave amplitudes is less than a predetermined number (YES in step S116), the process proceeds to step S118.

When determined that the number of changed pulse wave amplitudes reached the predetermined value (NO in step S116), the change processing unit 112 informs no-operation (step S120). Specifically, for example, a message "no further operation is possible" is displayed in a predetermined region of the second display region 40B. The process proceeds to step S122 after such process is finished. The predetermined number is preferably one. In such a case, the processes of steps S116 to S120 may not be performed.

In step S118, whether or not an instruction to end the operation is input by the user is determined. The instruction to end the operation may be to again push the determination switch 415. When determined that the instruction to end the operation is not input (NO in step S118), the process returns to step S112. When determined that the instruction to end the operation is input (YES in step S118), the process proceeds to step S122.

In step S122, the blood pressure calculating unit 106 calculates (estimates) the systolic blood pressure and the diastolic blood pressure as reference blood pressure values based on the pulse wave amplitude subsequent to the change. Specifically, the blood pressure calculating unit 106 calculates the reference blood pressure value based on the actual measurement amplitude data and the processed amplitude data AM#(1) other than the actual measurement amplitude data AM(k) of the pulse wave related information 90.

After the reference blood pressure value is calculated, the display processing unit 108 displays the reference blood pressure value and the pulse wave amplitude information subsequent to the change on the display unit 40 (step S124). The display example is shown in FIGS. 14A and 14B.

Figure 14:
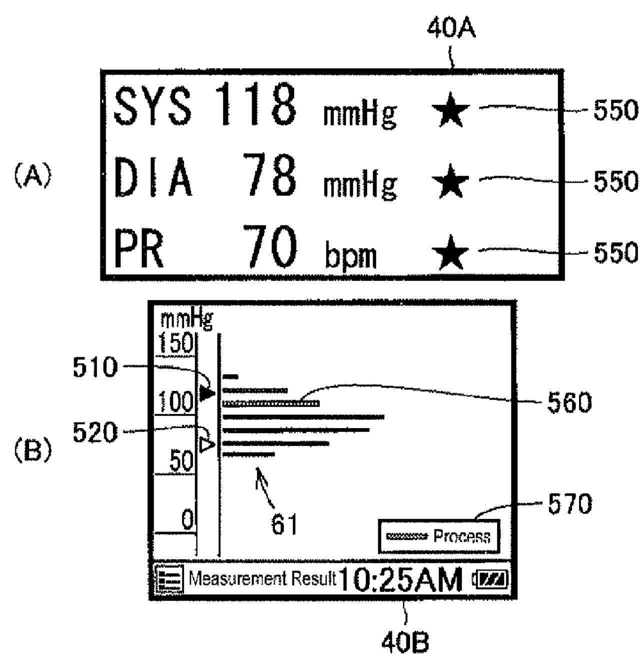
FIGS. 14A and 14B are views showing one example of a screen displayed in step S124 of FIG. 7.

With reference to FIG. 14A, the systolic blood pressure (SYS), the diastolic blood pressure (DIA), and the number of pulses (PR) are displayed in numerical values in the first display region 40A of the display unit 40, and marks 550 indicating that each numerical value is a reference value are displayed. With reference to FIG. 14B, second pulse wave amplitude information 61 is displayed in the second display region 40B. Specifically, the amplitude bar 560 indicating the processed pulse wave amplitude is displayed in an identifiable manner from the other amplitude bars. For instance, the non-processed amplitude bar may be displayed in black, and only the processed amplitude bar 560 may be displayed in red. Information 570 indicating that the red amplitude bar 560 is processed may also be displayed together.

In step S124, notification may be made that the blood pressure value being displayed is the reference blood pressure value with an LED (Light Emitting Diode) (not shown) or a buzzer in addition to or in place of the display of the marks 550.

Whether or not the OK instruction is input by the user is then determined (step S126). When determined that the OK instruction is not input (NO in step S126), the information of the pulse wave amplitude changed up to this point is reset (step S127) and the process returns to step S112. That is, in step S127, the processed amplitude data AM#(1) is cleared and "NULL" is recorded.

When determined that the OK instruction is input (YES in step S126), the CPU 100 stores the reference blood pressure value in the corresponding measurement result storage region of the flash memory 43 (step S128). In this case, the value of the identification flag F is "1", which means reference value.

The measurement and display process according to the present embodiment is then terminated.

As described above, since the medical staff can manually change the magnitude and/or the position of the pulse wave amplitude according to the present embodiment, the blood pressure value in which the noise is removed can be obtained without re-measuring the pulse wave (cuff pressure signal). As a result, the binding hour of the person to be measured (patient) can be reduced, and the examination time of the patient by the medical staff can be shortened.

The medical staff needs to recognize that processing is not being recommended by showing that the blood pressure value calculated based on the processed pulse wave amplitude is merely a reference value. In this regards, the blood pressure information display device 1 can also be considered as a diagnosis assisting device that assists the diagnosis of the medical staff on the person to be measured.

In the present embodiment, the pulse wave amplitude for every beat is displayed using bars and the change in length is accepted, but this mode is not the sole case. For instance, the pulse wave waveform subsequent to filtering may be displayed along the time axis and the shape thereof may be changed for every beat. FIGS. 15A to 15D are views showing examples in which the pulse wave waveform for one beat is shortened or deleted. FIGS. 15A to 15D each correspond to FIGS. 12A to 12D described above.

Figure 15:
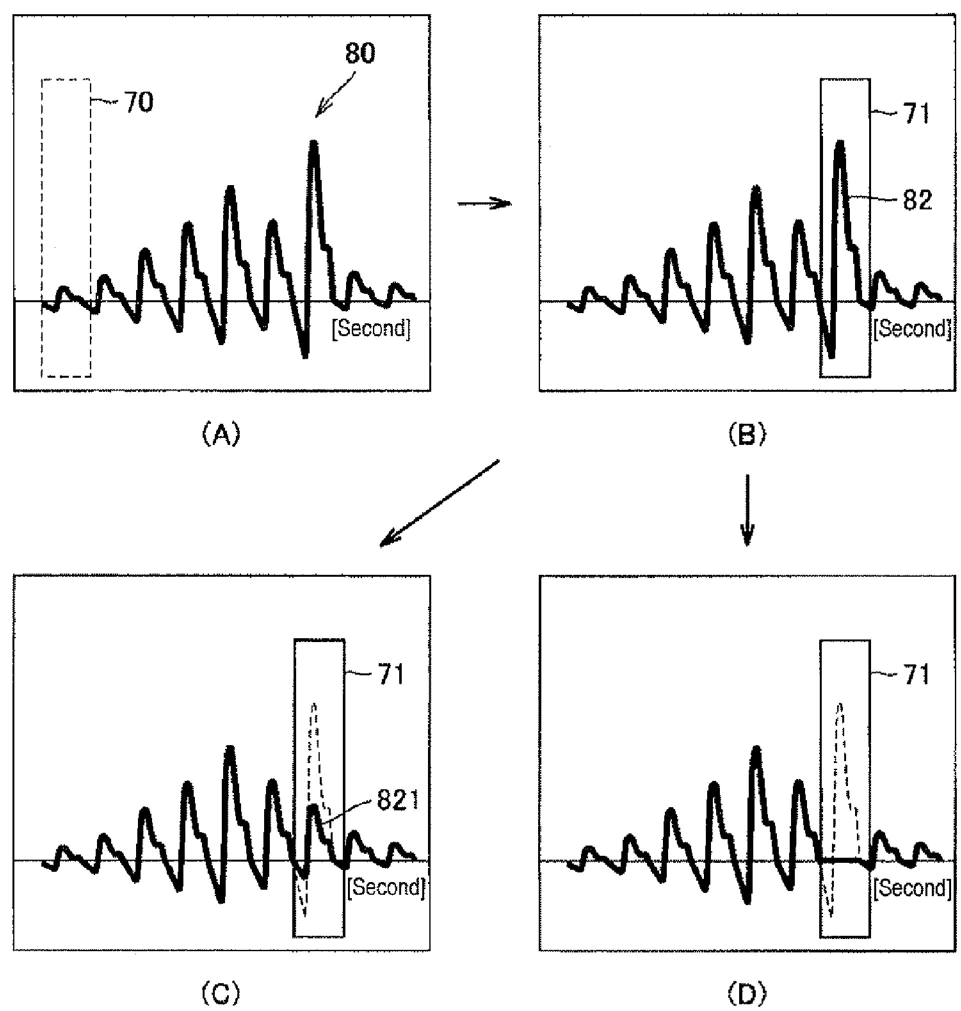
FIGS. 15A to 15D are views showing examples in which the pulse wave waveform for one beat is shortened or deleted.

In FIG. 15A, the pulse wave waveform along the time axis is displayed as first pulse wave amplitude information 80. That is, in the present embodiment, the "pulse wave amplitude information" may not be the pulse wave amplitude itself as long as it represents the magnitude and the position of the extracted pulse wave amplitude for every beat.

In FIG. 15B, a pulse wave 82 is selected as the changing target. In FIG. 15C, a pulse wave 821 shorted to about ⅓ of the original amplitude is shown. In FIG. 15D, the selected pulse wave 82 is deleted.

In the present embodiment, the processable number is limited, but the changing range of the magnitude of the pulse wave amplitude may be limited in addition to the processable number. For instance, the changing ratio with the original magnitude as a reference is preferably defined in advance. Specifically, about ⅓ to twice the original pulse wave amplitude is desirable.

In the present embodiment, the pulse wave amplitude to be changed of the plurality of extracted pulse wave amplitudes is selected and performed with the changing process, but the pulse wave amplitude having the magnitude corresponding to the instruction from the operation unit 41 may be added to the specified position (cuff pressure or time).

The blood pressure information display device 1 according to the present embodiment of a type installed in hospitals has been described, by way of example, but may be a portable type device as long as it is a device having a large display region. That is, the pulse wave (pulse wave measurement information) measured outside the hospital may be stored, and the medical staff may read out the stored pulse wave measurement information to perform the above-described operation. In this case, only the process of step S104 or the processes of steps S104 and S105 in the flowchart of FIG. 7 are separately performed through the operation of the person to be measured.

<Variant>

In the above-described embodiment, when the instruction to transition to the processing mode is input, the cursor is placed (surrounded with broken line frame 70) on the pulse wave amplitude at a predetermined position (e.g., uppermost position). Therefore, the medical staff has to move the cursor up to the position of the pulse wave amplitude to be changed.

In the variant of the present embodiment, on the other hand, the pulse wave amplitude that becomes the changing candidate is specified by detecting the noise superimposed on the pulse wave, and the cursor is placed on the specified pulse wave amplitude. The pulse wave amplitude to be changed thus can be immediately selected.

Only the portion different from the first embodiment will be described below.

Figure 16:
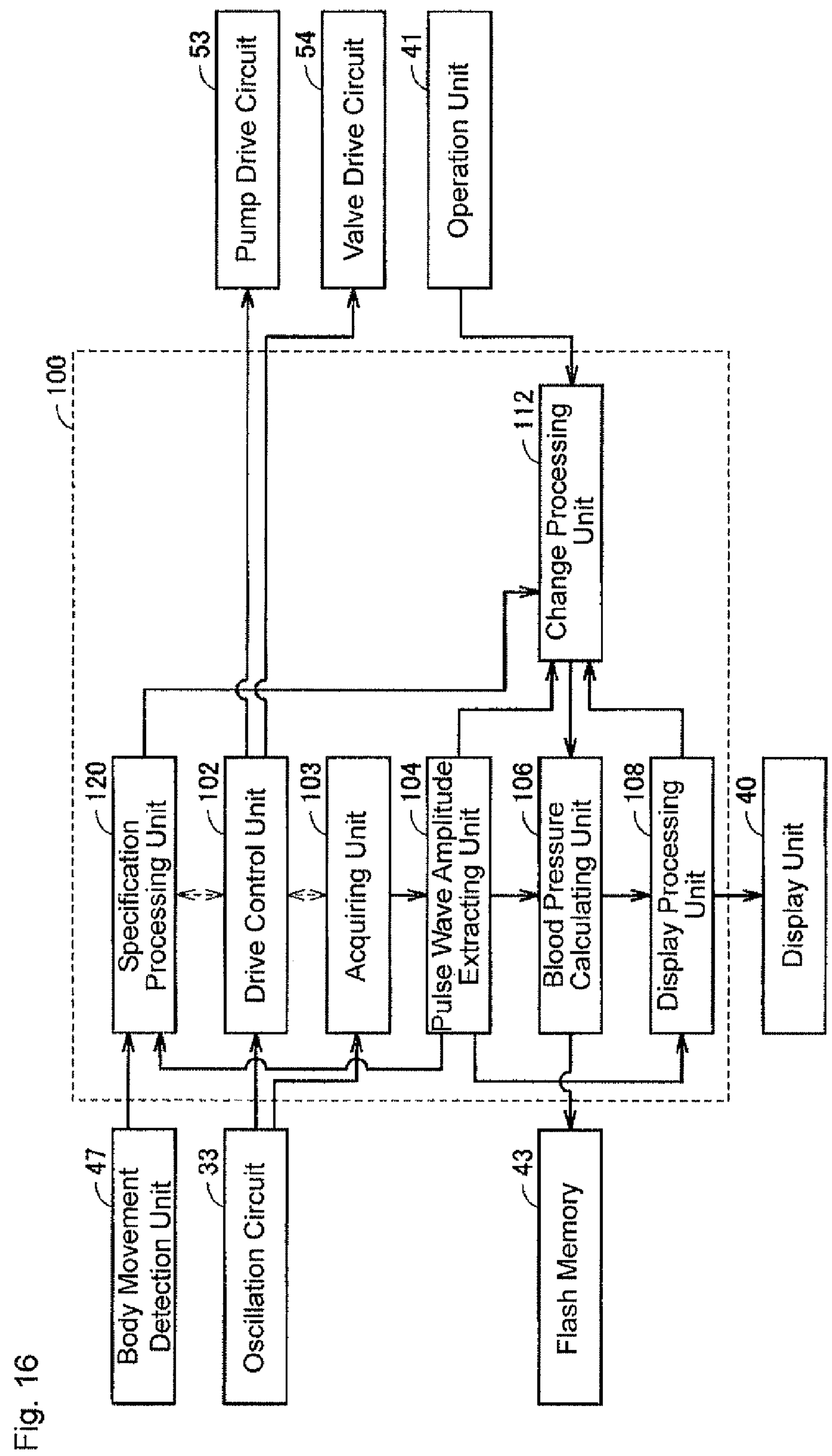
FIG. 16 is a function block diagram showing the function configuration of the blood pressure information display device according to a variant of the first embodiment of the present invention.

FIG. 16 is a function block diagram showing the function configuration of the blood pressure information display device 1 according to a variant of the first embodiment of the present invention. With reference to FIG. 16, the CPU 100 further includes a specification processing unit 120 in addition to the function blocks shown in FIG. 6.

The specification processing unit 120 applies the known noise detection algorithm existing from the related art to a plurality of pulse wave amplitudes extracted by the pulse wave amplitude extracting unit 104 to specify the pulse wave amplitude containing noise. The specification processing unit 120, for example, sets a flag in the field (not shown) of the same row as the specified pulse wave amplitude of the actual measurement amplitude data recorded in the item 93 of the pulse wave related information 90 of the memory 42. The pulse wave amplitude of the changing candidate is thereby specified.

Alternatively, the blood pressure information display device 1 may further include a hardware for detecting noise, and the specification processing unit 120 may specify the pulse wave amplitude containing noise by detecting the signal from the relevant hardware. Specifically, a body movement detection unit 47 for detecting the body movement of the person to be measured may be arranged in the cuff 20. The body movement detection unit 47 may be an acceleration sensor. In this case, the specification processing unit 120 acquires a signal from the body movement detection unit 47 while the process of the drive control unit 102 is being carried out. The pulse wave amplitude at the time point the body movement is detected is specified as the changing candidate.

The process of the specification processing unit 120 may be executed immediately before step S112 (select pulse wave amplitude), or may be executed before step S110 (detect instruction to transition to processing mode).

The change processing unit 112 selectably displays the pulse wave amplitude specified as the changing candidate at the time point the process proceeded to step S112 of FIG. 7. That is, the position of placing the cursor first is assumed as the position of the pulse wave amplitude specified as the changing candidate. More specifically, process is performed such that the amplitude bar corresponding to the specified pulse wave amplitude is surrounded with the broken line frame 70.

The changing process of the amplitude bar thus can be smoothly carried out since the cursor is placed at the position of the pulse wave amplitude that is the changing candidate.

The process of the specification processing unit 120 may be performed before step S108 (display result of actual measurement value), and the position of the pulse wave amplitude specified by the display processing unit 108 may be displayed so as to be identifiable from others in step S108. The medical staff then can more easily decide whether or not to transition to the processing mode.

When the specification processing nit 120 uses the noise detection algorithm, the magnitude of the pulse wave amplitude when the noise is removed from the specified pulse wave amplitude may be further displayed as a rough indication.

The specification processing unit 120 may also specify the area (time or cuff pressure value) where the pulse wave for one beat is missing using a known algorithm such as the noise detection algorithm. That is, the position where the pulse wave is assumed to originally exist may be specified even if the pulse wave does not exist in the measurement data. In this case, the change processing unit 112 may place the cursor on the specified position. Specifically, the broken line frame 70 may be displayed at the specified position (cuff pressure), and the pulse wave amplitude may be additionally displayed at the relevant position. In this case as well, the magnitude of the pulse wave amplitude that may exist at the specified position may be shown as a rough indication.

Second Embodiment

In the first embodiment and the variant described above, the blood pressure information display device performs both the pulse wave measurement process (acquisition of cuff pressure signal) and the blood pressure information display process. In the second embodiment of the present invention, on the other hand, each process is executed in a different device.

Only the portion different from the first embodiment will be described below.

Figure 17:
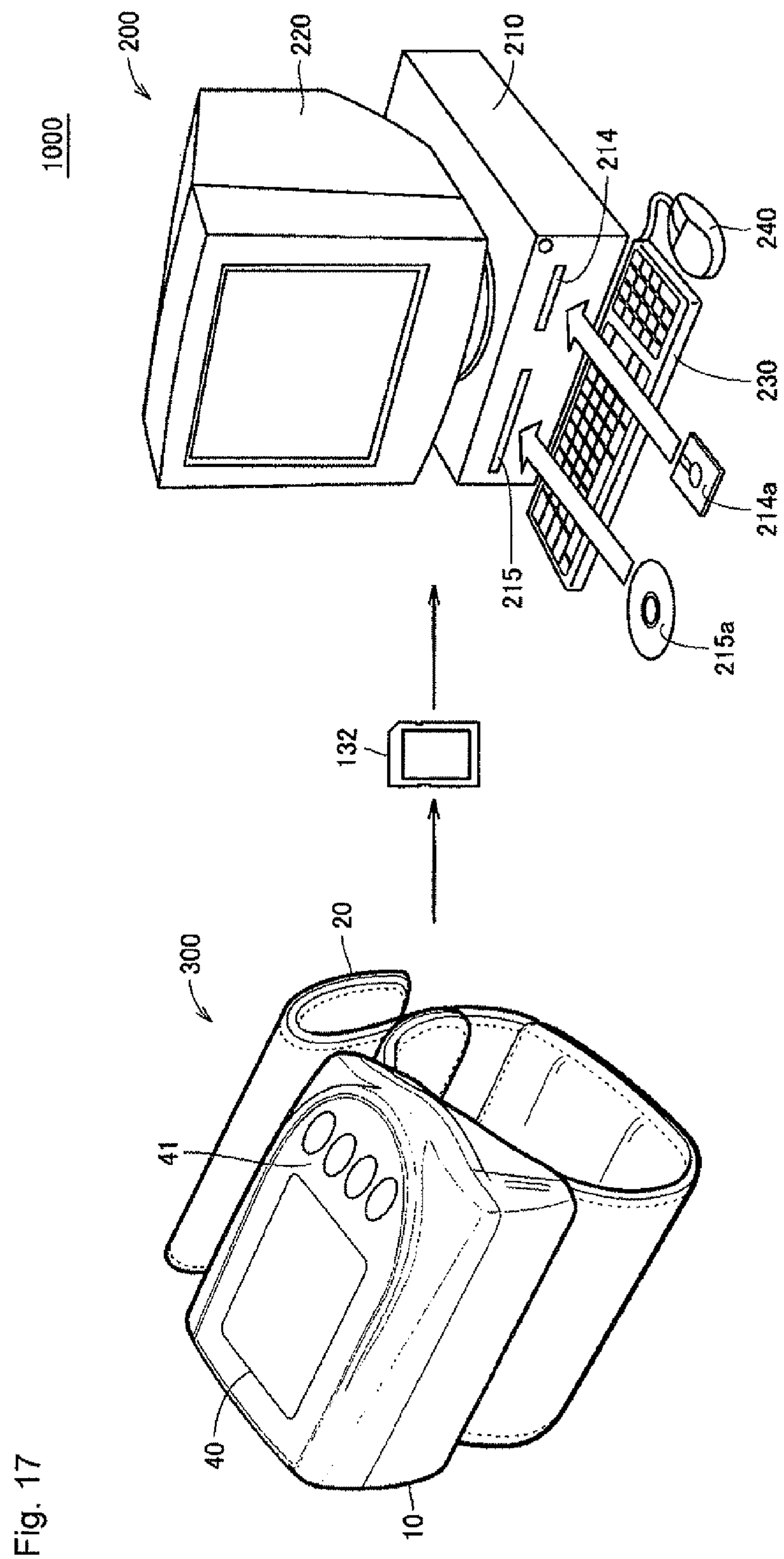
FIG. 17 is a view showing an outline of a blood pressure information display system according to a second embodiment of the present invention.

FIG. 17 is a view showing an outline of a blood pressure information display system 1000 according to a second embodiment of the present invention.

With reference to FIG. 17, the blood pressure information display system 1000 includes a pulse wave measurement device 300 and a blood pressure information display device 200. The pulse wave measurement device 300 is used in households such as outside hospitals. The pulse wave measurement device 300 records the pulse wave measurement information in a removable recording medium 132. The blood pressure information display device 200 reads out the pulse wave measurement information from the recording medium 132 to perform processes such as calculation and display of the blood pressure value, and changing of the pulse wave amplitude based on the pulse wave measured by the pulse wave measurement device 300.

The pulse wave measurement device 300 may be a portable sphygmomanometer. The hardware configuration of the pulse wave measurement device 300 is similar to the configuration shown in FIG. 5. However, the authentication information detection unit 48 and the cursor switch 41D may not be arranged. The blood pressure information display device 200 according to the present embodiment may be a general PC (Personal Computer).

Figure 18:
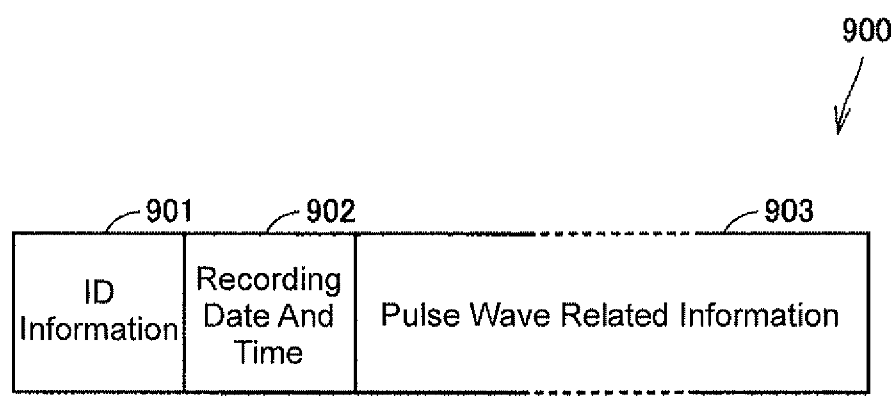
FIG. 18 is a view showing one example of a data structure of pulse wave measurement information recorded in the recording medium.

FIG. 18 is a view showing one example of a data structure of pulse wave measurement information 900 recorded in the recording medium 132. With reference to FIG. 18, the pulse wave measurement information 900 includes three fields 901 to 903, "ID information", "recording date and time", and "pulse wave related information" by way of example. Describing the content of each field, the "ID information" field 901 stores identification number and the like for specifying the pulse wave measurement information, and the "recording date and time" field 902 stores information such as measurement date and time and measurement period timed by the timing unit 45. The "pulse wave related information" field 903 stores, for example, actual measurement information 95 of the pulse wave related information 90 shown in FIG. 8.

Figure 19:
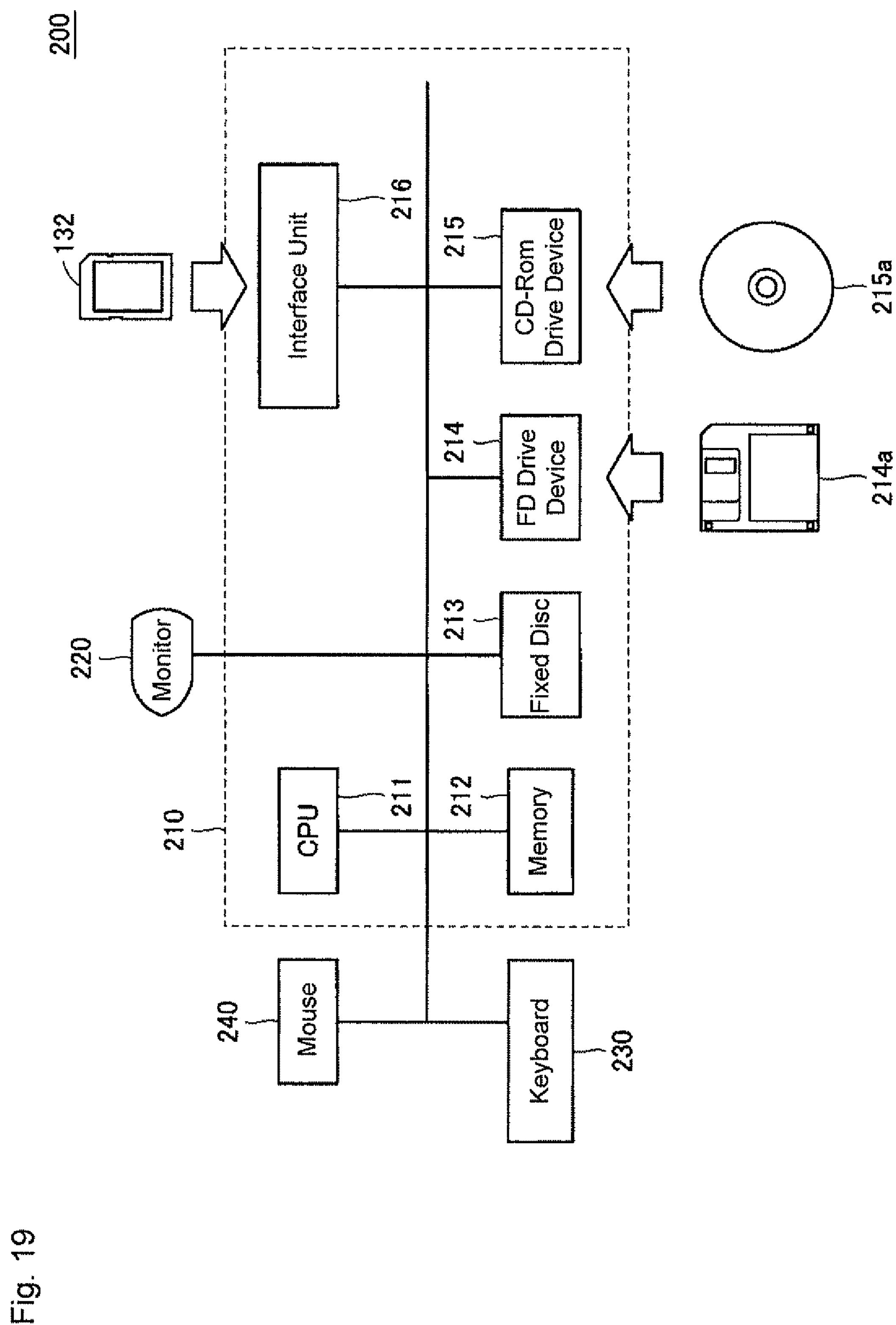
FIG. 19 is a hardware block diagram showing one example of the hardware configuration of the blood pressure information display device according to the second embodiment of the present invention.

FIG. 19 is a hardware block diagram showing one example of the hardware configuration of the blood pressure information display device 200.

With reference to FIG. 19, the blood pressure information display device 200 includes a main body 210, a monitor 220, a keyboard 230, and a mouse 240, where the main body 210 includes a CPU 211, a memory 212, a fixed disc 213 serving as a storage device, an FD (Flexible Disk) drive device 214, a CD-ROM (Compact Disk-Read Only Memory) drive device 215, and an interface section 216. Such hardware is mutually connected with a bus.

An FD 214*a* is attached to the FD drive device 214, and a CD-ROM 215*a* is attached to the CD-RPM drive device 215. The blood pressure information display device 200 according to the present embodiment is realized when the CPU 211 executes a software using the hardware such as the memory 212. Such software is generally stored in a recording medium such as the FD 214*a* or the CD-ROM 215*a*, or is distributed through the network and the like. Such software is read from the recording medium by the FD drive device 214, the CD-ROM drive device 215, and the like, or is received at the communication interface (not shown) and stored in the fixed disc 213. Furthermore, the software is read out from the fixed disc 213 to the memory 212 and executed by the CPU 211.

The monitor 220 is a display unit for displaying information such as the blood pressure output by the CPU 211, and is configured by an LCD (Liquid Crystal Display), a CRT (Cathode Ray Tube), and the like by way of example. The mouse 240 accepts commands from the user (medical staff, representatively person who makes diagnosis such as doctors) corresponding to the operation of click, slide, and the like. The keyboard 230 accepts commands from the user corresponding to the input key. The CPU 211 is an arithmetic processing unit for performing various types of operations by sequentially executing the programmed command. The memory 212 stores various types of information according to the program execution of the CPU 211. The interface unit 216 is a site for receiving the pulse wave measurement information 900 by the pulse wave measurement device 300, and is configured by a slot to which the recording medium 132 can be attached, a peripheral circuit for controlling the slot, and the like in the present embodiment. The interface unit 216 may be configured as a communication interface unit capable of data communicating with the pulse wave measurement device 300 in place of the slot to which the recording medium 132 can be attached. The fixing disc 213 is a non-volatile storage device for storing programs to be executed by the CPU 212, and the pulse wave measurement information 900 received from the pulse wave measurement device 300. Other output devices such as a printer may be connected to the blood pressure information display device 200, as necessary.

The CPU 211 performs the control of the calculation, display and the like of the blood pressure value based on the pulse wave measurement information 900 stored in the fixed disc 213.

The CPU 100 of the pulse wave measurement device 300 includes at least the functions of the drive control unit 102 and the acquiring unit 103 of the function blocks of the first embodiment shown in FIG. 6. In the present embodiment, the function of the pulse wave amplitude extracting unit 104 is also provided. Specifically, the CPU 100 executes steps S104 and S105 (acquisition of cuff pressure signal and extraction of pulse wave amplitude) of the flowchart of FIG. 7. The data acquired through such processes are then recorded in the recording medium 132 as pulse wave measurement information 900.

The CPU 211 of the blood pressure information display device 200 includes at least the functions of the blood pressure calculating unit 106, the display processing unit 108, and the change processing unit 112 of the function blocks of the first embodiment shown in FIG. 6. The CPU 211 may also include the function of the pulse wave amplitude extracting unit 104. The CPU 211 first reads out the pulse wave related information 903 of the pulse wave measurement information 900 from the fixed disc 213, and executes the processes after step S106 (calculation of actual measurement blood pressure value) of the flowchart of FIG. 7.

The blood pressure information display method performed by the blood pressure information display device 1, 200 described above may be provided as a program. The program according to the present invention may be to call out the necessary module of the program module provided as one part of an operating system (OS) of the computer with a predetermined array and at a predetermined timing and to process the same. In this case, the module is not included in the program itself, and the process is executed in cooperation with the OS. Such program that does not include the module is also encompassed in the program according to the present invention.

The program according to the present invention may be provided by being incorporated as part of another program. In this case as well, the module included in another program is not included in the program itself, and the process is executed in cooperation with the other program. The program incorporated in another program is also encompassed in the program according to the present invention.

The embodiments disclosed herein are illustrative in all aspects and should not be construed as being restrictive. The scope of the invention is defined by the Claims rather than by the description made above, and all modifications equivalent in meaning with the Claims and within the scope thereof are intended to be encompassed therein.

DESCRIPTION OF SYMBOLS

1 blood pressure information display device
10 main body
20 cuff
21 air bag
20 air system
31 air tube
32 pressure sensor
33 oscillation circuit
40 display unit
41 operation unit
41A power switch
41B measurement switch
41C set switch
41D cursor switch
42 memory
43 flash memory
44 power supply
45 timing unit
46 data input/output unit
47 body movement detection unit
48 authentication information detection unit
50 adjustment unit
51 pump
52 valve
53 pump drive circuit
54 valve drive circuit
90 pulse wave related information
100 CPU
102 drive control unit
103 acquiring unit
104 pulse wave amplitude extracting unit
106 blood pressure calculating unit
108 display processing unit
112 change processing unit
120 specification processing unit
132 recording medium
200 blood pressure information display device
210 main body
211 CPU
212 memory
213 fixed disc
214 FD drive device
215 CD-ROM drive device
216 interface unit
220 monitor
230 keyboard
240 mouse
300 pulse wave measurement device
411 leftward switch
412 rightward switch
413 upward switch
414 downward switch
415 determination switch
900 pulse wave measurement information

The invention claimed is:

1. A blood pressure information display device for calculating a blood pressure value, and displaying the calculated blood pressure value as blood pressure information, the blood pressure information display device comprising:

a display unit;

an operation unit for accepting an operation by a user;

a cuff to be wrapped around a predetermined measurement site of a person to be measured;

an adjustment unit for adjusting an inner pressure of the cuff;

a pressure detection unit for detecting a cuff pressure signal representing the pressure in the cuff;

an acquiring unit for acquiring the cuff pressure signal in time-series from the pressure detection unit when a drive control of the adjustment unit is being carried out;

an extracting unit for extracting a pulse wave amplitude for every beat based on the cuff pressure signal;

a display processing unit for displaying pulse wave amplitude information representing a plurality of extracted pulse wave amplitudes on the display unit;

a change processing unit for performing a process of changing a magnitude of a specified pulse wave amplitude of the plurality of extracted pulse wave amplitudes according to an instruction from the operation unit when a predetermined instruction is input from the operation unit; and a calculating unit for calculating a reference blood pressure value by applying a predetermined algorithm to a plurality of pulse wave amplitudes reflecting the change on the specified pulse wave amplitude; wherein the display processing unit displays the reference blood pressure value on the display unit as the blood pressure information.

2. The blood pressure information display device according to claim 1, further comprising a storage unit for storing the plurality of extracted pulse wave amplitudes in association with at least one of a cuff pressure or a time, and for storing an amplitude value subsequent to the specified pulse wave amplitude being changed in association with a cuff pressure or a time at which the specified pulse wave amplitude is detected.

3. The blood pressure information display device according to claim 2, wherein the display processing unit displays the plurality of extracted pulse wave amplitudes along a cuff pressure axis or a time axis as the pulse wave amplitude information.

4. The blood pressure information display device according to claim 3, wherein the change processing unit changes a position of the specified pulse wave amplitude on the cuff pressure axis or the time axis according to the instruction from the operation unit.

5. The blood pressure information display device according to claim 3, wherein the change processing unit adds a pulse wave amplitude having a magnitude corresponding to an instruction to a specified position on the cuff pressure axis or the time axis according to the instruction from the operation unit.

6. The blood pressure information display device according to claim 1, wherein the change processing unit accepts the specification of change for only a predetermined number of pulse wave amplitudes.

7. The blood pressure information display device according to claim 1, wherein the change processing unit accepts an instruction to change only within a predetermined range of an original magnitude for the specified pulse wave amplitude.

8. The blood pressure information display device according to claim 1, wherein the display processing unit further notifies that the reference blood pressure value is a reference value.

9. The blood pressure information display device according to claim 1, wherein the calculating unit calculates an actual measurement blood pressure value by applying the predetermined algorithm to the plurality of extracted pulse wave amplitudes; and the display processing unit further displays the actual measurement blood pressure value along with the pulse wave amplitude information.

10. The blood pressure information display device according to claim 1, further comprising:

a specification processing unit for specifying at least one of the plurality of extracted pulse wave amplitudes as a changing candidate by detecting noise; wherein the display processing unit displays the specified pulse wave amplitude so as to be selectable.

11. The blood pressure information display device according to claim 1, further comprising:

an authentication information detection unit for detecting authentication information for authenticating the user; wherein the change processing unit executes a changing process of the plurality of extracted pulse wave amplitudes only when the user is authenticated based on the authentication information detected by the authentication information detection unit.

12. A blood pressure information display system comprising a pulse wave measurement device and a blood pressure information display device, wherein the pulse wave measurement device includes, a cuff to be wrapped around a predetermined measurement site of a person to be measured, an adjustment unit for adjusting an inner pressure of the cuff, a pressure detection unit for detecting a cuff pressure signal representing the pressure in the cuff, and an acquiring unit for acquiring the cuff pressure signal in time-series from the pressure detection unit when a drive control of the adjustment unit is being carried out; and the blood pressure information display device includes, a display unit, an operation unit for accepting an operation by a user, a display processing unit for displaying pulse wave amplitude information representing a plurality of pulse wave amplitudes extracted based on the cuff pressure signal in time-series on the display unit, a change processing unit for performing a process of changing a magnitude of a specified pulse wave amplitude of the plurality of extracted pulse wave amplitudes according to an instruction from the operation unit when a predetermined instruction is input from the operation unit, and a calculating unit for calculating a reference blood pressure value by applying a predetermined algorithm to a plurality of pulse wave amplitudes reflecting the change on the specified pulse wave amplitude; and the display processing unit displays the reference blood pressure value on the display unit as the blood pressure information.

13. A blood pressure information display method for calculating a blood pressure value, and displaying the calculated blood pressure value as blood pressure information, a central processing unit executing the method steps of:

displaying pulse wave amplitude information representing a plurality of pulse wave amplitudes extracted from a pulse wave measured in a process of gradually changing a cuff pressure;

changing a magnitude of a specified pulse wave amplitude of the plurality of extracted pulse wave amplitudes according to an instruction from a user when a predetermined instruction is input:

calculating a reference blood pressure value by applying a predetermined algorithm to the plurality of pulse wave amplitudes subsequent to the change; and displaying the reference blood pressure value as the blood pressure information.

14. A non-transitory recording medium recorded with a blood pressure information display program for calculating a blood pressure value, and displaying the calculated blood pressure value as blood pressure information, the program causing a computer to execute the steps of:

displaying pulse wave amplitude information representing a plurality of pulse wave amplitudes extracted from a pulse wave measured in a process of gradually changing a cuff pressure;

changing a magnitude of a specified pulse wave amplitude of the plurality of extracted pulse wave amplitudes according to an instruction from a user when a predetermined instruction is input;

calculating a reference blood pressure value by applying a predetermined algorithm to the plurality of pulse wave amplitudes subsequent to the change; and displaying the reference blood pressure value as the blood pressure information.

* * * * *